United States Patent
Gustafsson

(10) Patent No.: US 12,003,925 B2
(45) Date of Patent: Jun. 4, 2024

(54) MAGNETIC RETENTION SYSTEM

(71) Applicant: Cochlear Limited, Macquarie University (AU)

(72) Inventor: Johan Gustafsson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 18/072,758

(22) Filed: Dec. 1, 2022

(65) Prior Publication Data

US 2023/0156416 A1    May 18, 2023

Related U.S. Application Data

(63) Continuation of application No. 17/387,551, filed on Jul. 28, 2021, which is a continuation of application No. 16/148,146, filed on Oct. 1, 2018, now Pat. No. 11,082,783, which is a continuation of application No. 14/811,138, filed on Jul. 28, 2015, now Pat. No. 10,091,594.

(60) Provisional application No. 62/030,319, filed on Jul. 29, 2014.

(51) Int. Cl.
*H04R 25/00* (2006.01)
*A61N 1/36* (2006.01)

(52) U.S. Cl.
CPC ........ *H04R 25/606* (2013.01); *A61N 1/36036* (2017.08); *H04R 2209/022* (2013.01); *H04R 2225/67* (2013.01); *H04R 2460/13* (2013.01)

(58) Field of Classification Search
CPC .. H04R 2225/67; H04R 25/606; H04R 25/00; H04R 9/025
See application file for complete search history.

(56) References Cited

U.S. PATENT DOCUMENTS

| | | |
|---|---|---|
| 3,043,000 A | 7/1962 | Hatfield |
| 3,487,403 A | 12/1969 | Pihl |
| 3,573,812 A | 4/1971 | Pihl |
| D227,118 S | 6/1973 | Muraoka |

(Continued)

FOREIGN PATENT DOCUMENTS

| | | |
|---|---|---|
| AU | 2009101370 A4 | 3/2013 |
| CN | 2411869 Y | 12/2000 |

(Continued)

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.

(Continued)

*Primary Examiner* — Thaddeus B Cox
*Assistant Examiner* — Joshua Daryl D Lannu
(74) *Attorney, Agent, or Firm* — Pilloff Passino & Cosenza LLP; Martin J. Cosenza

(57) ABSTRACT

An external component of a medical device, including an actuator including a static magnetic flux path that reacts with a dynamic magnetic flux path to actuate the actuator, and a magnetic retention system configured to retain the external component to a recipient via interaction with a ferromagnetic component attached to a recipient, the magnetic retention system including a magnetic flux path that encircles the static magnetic flux path of the actuator.

36 Claims, 15 Drawing Sheets

(56) References Cited

U.S. PATENT DOCUMENTS

| | | |
|---|---|---|
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |
| 4,038,990 A | 8/1977 | Thompson |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| 4,352,960 A | 10/1982 | Dormer et al. |
| D267,541 S | 1/1983 | Kanemitsu |
| 4,414,701 A | 11/1983 | Johnson |
| 4,596,971 A | 6/1986 | Hirabayashi et al. |
| 4,606,329 A | 8/1986 | Hough |
| 4,610,621 A | 9/1986 | Taber et al. |
| 4,628,907 A | 12/1986 | Epley |
| 4,634,191 A | 1/1987 | Studer |
| 4,676,772 A | 6/1987 | Hooven |
| 4,726,378 A | 2/1988 | Kaplan |
| 4,731,718 A | 3/1988 | Sheu |
| 4,736,747 A | 4/1988 | Drake |
| 4,743,264 A | 5/1988 | Sherva-Parker |
| 4,792,368 A | 12/1988 | Sagawa et al. |
| 4,817,607 A | 4/1989 | Tatge |
| RE32,947 E | 6/1989 | Dormer et al. |
| 4,868,530 A | 9/1989 | Ahs |
| 4,917,504 A | 4/1990 | Scott et al. |
| 4,918,745 A | 4/1990 | Hutchison |
| 4,920,679 A | 5/1990 | Sarles et al. |
| 5,014,592 A | 5/1991 | Zweig et al. |
| 5,015,224 A | 5/1991 | Maniglia |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,282,858 A | 2/1994 | Bisch et al. |
| 5,314,453 A | 5/1994 | Jeutter |
| D348,067 S | 6/1994 | Lucey et al. |
| 5,338,287 A | 8/1994 | Miller et al. |
| 5,360,388 A | 11/1994 | Spindel et al. |
| 5,423,317 A | 6/1995 | Ijima et al. |
| 5,456,654 A | 10/1995 | Ball |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,716,407 A | 2/1998 | Knapp et al. |
| 5,746,897 A | 5/1998 | Heimanson et al. |
| 5,749,912 A | 5/1998 | Zhang et al. |
| 5,757,183 A | 5/1998 | Smith et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,913,815 A | 6/1999 | Ball et al. |
| 5,945,762 A | 8/1999 | Chen et al. |
| 5,965,282 A | 10/1999 | Baermann |
| 5,971,334 A | 10/1999 | Crawshaw et al. |
| 6,040,762 A | 3/2000 | Tompkins |
| 6,073,973 A | 6/2000 | Boscaljon et al. |
| 6,101,417 A | 8/2000 | Vogel et al. |
| 6,138,681 A | 10/2000 | Chen et al. |
| 6,157,278 A | 12/2000 | Katznelson et al. |
| 6,157,281 A | 12/2000 | Katznelson et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Faltys et al. |
| 6,313,551 B1 | 11/2001 | Hazelton |
| 6,348,070 B1 | 2/2002 | Teissl et al. |
| 6,355,998 B1 | 3/2002 | Schöb et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 | 1/2003 | Woods |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,643,378 B2 | 11/2003 | Schumaier |
| 6,668,065 B2 | 12/2003 | Lee et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,038,565 B1 | 5/2006 | Chell |
| 7,091,806 B2 | 8/2006 | Zimmerling et al. |
| 7,190,247 B2 | 3/2007 | Zimmerling |
| 7,191,007 B2 | 3/2007 | Desai et al. |
| 7,200,504 B1 | 4/2007 | Fister |
| 7,225,028 B2 | 5/2007 | Della Santina et al. |
| 7,231,252 B2 | 6/2007 | Duncan et al. |
| 7,266,208 B2 | 9/2007 | Charvin et al. |
| 7,338,028 B2 | 3/2008 | Zimmerling et al. |
| 7,386,143 B2 | 6/2008 | Easter et al. |
| 7,532,937 B2 | 5/2009 | Horio et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |
| 7,762,998 B2 | 7/2010 | Birk et al. |
| 7,808,348 B2 | 10/2010 | Fullerton et al. |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,246,533 B2 | 8/2012 | Chang et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,400,038 B2 | 3/2013 | Smith et al. |
| 8,406,443 B2 | 3/2013 | Westerkull et al. |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 | 1/2014 | Zimmerling et al. |
| 8,734,475 B2 | 5/2014 | Ekvall et al. |
| 8,744,106 B2 | 6/2014 | Ball |
| 8,758,394 B2 | 6/2014 | Zimmerling et al. |
| 8,768,480 B2 | 7/2014 | Charvin |
| 8,811,643 B2 | 8/2014 | Crawford et al. |
| 8,829,462 B2 | 9/2014 | Clarke et al. |
| 8,829,752 B2 | 9/2014 | Chen et al. |
| 8,897,475 B2 | 11/2014 | Ball et al. |
| 8,983,102 B2 | 3/2015 | Crawford et al. |
| 8,987,951 B2 | 3/2015 | Park |
| 9,002,469 B2 | 4/2015 | D'Ambrosio |
| 9,014,782 B2 | 4/2015 | Miyoshi |
| 9,022,917 B2 | 5/2015 | Kasic et al. |
| 9,042,995 B2 | 5/2015 | Dinsmoor et al. |
| 9,058,962 B2 | 6/2015 | Endo et al. |
| 9,113,268 B2 | 8/2015 | Ball et al. |
| RE45,701 E | 9/2015 | Zimmerling et al. |
| 9,136,728 B2 | 9/2015 | Dinsmoor et al. |

(56) References Cited

U.S. PATENT DOCUMENTS

| | | |
|---|---|---|
| 9,144,676 B2 | 9/2015 | Gibson et al. |
| 9,179,228 B2 | 11/2015 | Ruppersberg et al. |
| 9,210,521 B2 | 12/2015 | Kasic et al. |
| 9,258,656 B2 | 2/2016 | Ruppersberg et al. |
| 9,392,384 B2 | 7/2016 | Crawford et al. |
| 9,420,388 B2 | 8/2016 | Ball |
| 9,526,810 B2 | 12/2016 | Ruppersberg |
| 9,627,120 B2 | 4/2017 | Scott et al. |
| 9,736,601 B2 | 8/2017 | Kasic et al. |
| 9,739,842 B2 | 8/2017 | Holm et al. |
| 9,788,125 B2 | 10/2017 | Ruppersberg et al. |
| RE46,624 E | 12/2017 | Zimmerling et al. |
| 9,872,115 B2 | 1/2018 | Kennes |
| 9,872,993 B2 | 1/2018 | Zimmerling |
| 10,130,807 B2 | 11/2018 | Leigh et al. |
| 10,186,360 B2 | 1/2019 | Shimbo et al. |
| 10,405,891 B2 | 9/2019 | Pool et al. |
| 10,646,712 B2 | 5/2020 | Smith et al. |
| 10,917,730 B2 | 2/2021 | Kennes et al. |
| 10,942,042 B2 | 3/2021 | Bidaux et al. |
| 11,012,796 B2 | 5/2021 | Andersson et al. |
| 11,097,095 B2 | 8/2021 | Smith et al. |
| 2001/0021805 A1 | 9/2001 | Blume et al. |
| 2002/0076071 A1 | 6/2002 | Single |
| 2002/0103430 A1 | 8/2002 | Hastings |
| 2002/0116033 A1 | 8/2002 | Greatbatch et al. |
| 2002/0116034 A1 | 8/2002 | Miller et al. |
| 2002/0120332 A1 | 8/2002 | Law et al. |
| 2003/0034039 A1 | 2/2003 | Schmid et al. |
| 2003/0034705 A1 | 2/2003 | Hakansson |
| 2003/0089933 A1 | 5/2003 | Janesky et al. |
| 2003/0120202 A1 | 6/2003 | Gordon |
| 2003/0139782 A1 | 7/2003 | Duncan |
| 2003/0161481 A1 | 8/2003 | Miller et al. |
| 2003/0161482 A1 | 8/2003 | Miller et al. |
| 2003/0163021 A1 | 8/2003 | Miller et al. |
| 2003/0163022 A1 | 8/2003 | Miller et al. |
| 2003/0171787 A1 | 9/2003 | Money et al. |
| 2003/0171792 A1 | 9/2003 | Zarinetchi et al. |
| 2003/0181956 A1 | 9/2003 | Duncan et al. |
| 2004/0012470 A1 | 1/2004 | Zimmerling et al. |
| 2004/0032962 A1 | 2/2004 | Westerkull |
| 2004/0059423 A1 | 3/2004 | Barnes et al. |
| 2004/0136558 A1 | 7/2004 | Usuki et al. |
| 2004/0147804 A1 | 7/2004 | Schneider et al. |
| 2004/0148025 A1 | 7/2004 | Schneider et al. |
| 2004/0260361 A1 | 12/2004 | Gibson |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0070346 A1 | 3/2005 | Pan |
| 2005/0101830 A1 | 5/2005 | Easter et al. |
| 2005/0159791 A1 | 7/2005 | Daly et al. |
| 2005/0165471 A1 | 7/2005 | Wang et al. |
| 2005/0171579 A1 | 8/2005 | Tasche et al. |
| 2005/0197715 A1 | 9/2005 | Kugler et al. |
| 2005/0216075 A1 | 9/2005 | Wang et al. |
| 2005/0228214 A1 | 10/2005 | Schneider et al. |
| 2005/0228215 A1 | 10/2005 | Schneider et al. |
| 2005/0240098 A1 | 10/2005 | Zhong et al. |
| 2006/0030905 A1 | 2/2006 | Malaver |
| 2006/0045298 A1 | 3/2006 | Westerkull |
| 2006/0056649 A1 | 3/2006 | Schumaier |
| 2006/0084857 A1 | 4/2006 | Massengill et al. |
| 2006/0119356 A1 | 6/2006 | Rabe et al. |
| 2006/0184212 A1 | 8/2006 | Faltys et al. |
| 2006/0217792 A1 | 9/2006 | Hussein et al. |
| 2006/0241746 A1 | 10/2006 | Shaoulian et al. |
| 2006/0244560 A1 | 11/2006 | Zimmerling et al. |
| 2006/0247488 A1 | 11/2006 | Waldmann |
| 2007/0053536 A1 | 3/2007 | Westerkull |
| 2007/0083078 A1 | 4/2007 | Easter et al. |
| 2007/0100197 A1 | 5/2007 | Perkins et al. |
| 2007/0126540 A1 | 6/2007 | Zimmerling |
| 2007/0170533 A1 | 7/2007 | Doogue et al. |
| 2007/0179333 A1 | 8/2007 | Bove |
| 2007/0208403 A1 | 9/2007 | Della Santina et al. |
| 2008/0009920 A1 | 1/2008 | Gibson et al. |
| 2008/0044049 A1 | 2/2008 | Ho et al. |
| 2008/0071353 A1 | 3/2008 | Weber et al. |
| 2008/0221641 A1 | 9/2008 | Hochmair |
| 2008/0293998 A1 | 11/2008 | Andrews |
| 2008/0304686 A1 | 12/2008 | Meskens et al. |
| 2009/0030529 A1 | 1/2009 | Berrang et al. |
| 2009/0043149 A1 | 2/2009 | Abel |
| 2009/0069869 A1 | 3/2009 | Stouffer et al. |
| 2009/0138062 A1 | 5/2009 | Balslev |
| 2009/0237080 A1 | 9/2009 | Kato et al. |
| 2009/0248155 A1 | 10/2009 | Parker |
| 2009/0251264 A1 | 10/2009 | Fullerton et al. |
| 2009/0281367 A1 | 11/2009 | Cho et al. |
| 2009/0287036 A1 | 11/2009 | Shapiro et al. |
| 2009/0287278 A1 | 11/2009 | Charvin |
| 2009/0295521 A1 | 12/2009 | Fullerton et al. |
| 2010/0145135 A1 | 6/2010 | Ball et al. |
| 2010/0219712 A1 | 9/2010 | Kogure et al. |
| 2010/0237969 A1 | 9/2010 | Crawshaw |
| 2010/0272299 A1 | 10/2010 | Van Schuylenbergh et al. |
| 2010/0292759 A1 | 11/2010 | Hahn et al. |
| 2011/0004278 A1 | 1/2011 | Aghassian |
| 2011/0022120 A1 | 1/2011 | Ball et al. |
| 2011/0031839 A1 | 2/2011 | Fullerton et al. |
| 2011/0054237 A1 | 3/2011 | Shapiro et al. |
| 2011/0077502 A1 | 3/2011 | Rofougaran |
| 2011/0106210 A1 | 5/2011 | Meskens |
| 2011/0112607 A1 | 5/2011 | Zierhofer |
| 2011/0130622 A1 | 6/2011 | Ilberg |
| 2011/0152603 A1 | 6/2011 | Perkins et al. |
| 2011/0224789 A1 | 9/2011 | Griffith |
| 2011/0264172 A1 | 10/2011 | Zimmerling et al. |
| 2011/0268303 A1 | 11/2011 | Ahsani |
| 2011/0285488 A1 | 11/2011 | Scott et al. |
| 2011/0291507 A1 | 12/2011 | Post |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0062992 A1 | 3/2012 | Kimoto |
| 2012/0078035 A1 | 3/2012 | Andersson et al. |
| 2012/0080039 A1 | 4/2012 | Siegert |
| 2012/0088956 A1 | 4/2012 | Asnes et al. |
| 2012/0095283 A1 | 4/2012 | Andersson et al. |
| 2012/0104875 A1 | 5/2012 | Park |
| 2012/0108887 A1 | 5/2012 | Vermeiren |
| 2012/0172659 A1 | 7/2012 | Ball et al. |
| 2012/0237067 A1 | 9/2012 | Asnes |
| 2012/0238799 A1 | 9/2012 | Ball et al. |
| 2012/0256715 A1 | 10/2012 | Fullerton et al. |
| 2012/0262019 A1 | 10/2012 | Smith et al. |
| 2012/0262020 A1 | 10/2012 | Smith et al. |
| 2012/0284969 A1 | 11/2012 | Fullerton et al. |
| 2012/0296155 A1 | 11/2012 | Ball |
| 2012/0313473 A1 | 12/2012 | Chen et al. |
| 2012/0319809 A1 | 12/2012 | Fullerton |
| 2012/0323066 A1 | 12/2012 | Cho et al. |
| 2012/0330378 A1 | 12/2012 | Crawford et al. |
| 2013/0004003 A1 | 1/2013 | Tada |
| 2013/0006044 A1 | 1/2013 | Menzl |
| 2013/0018218 A1 | 1/2013 | Haller et al. |
| 2013/0023954 A1 | 1/2013 | Meskens |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0096366 A1 | 4/2013 | Bervoets et al. |
| 2013/0099703 A1 | 4/2013 | Epstein et al. |
| 2013/0110198 A1 | 5/2013 | Stoffaneller |
| 2013/0114834 A1 | 5/2013 | Bern |
| 2013/0165738 A1 | 6/2013 | Ball et al. |
| 2013/0190552 A1 | 7/2013 | Leblans |
| 2013/0195304 A1 | 8/2013 | Andersson |
| 2013/0199031 A1 | 8/2013 | Fullerton et al. |
| 2013/0202140 A1 | 8/2013 | Asnes |
| 2013/0207760 A1 | 8/2013 | Clarke et al. |

(56) References Cited

U.S. PATENT DOCUMENTS

| | | |
|---|---|---|
| 2013/0214631 A1 | 8/2013 | Smith et al. |
| 2013/0261701 A1 | 10/2013 | Kuratle et al. |
| 2013/0268012 A1 | 10/2013 | Sison |
| 2013/0278254 A1 | 10/2013 | Reeder et al. |
| 2013/0281764 A1 | 10/2013 | Björn et al. |
| 2013/0289384 A1 | 10/2013 | Jenison et al. |
| 2013/0305522 A1 | 11/2013 | Fullerton et al. |
| 2014/0005522 A1 | 1/2014 | Zurovcik |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0064531 A1 | 3/2014 | Andersson et al. |
| 2014/0094876 A1 | 4/2014 | Wingeier et al. |
| 2014/0121447 A1 | 5/2014 | Kasic et al. |
| 2014/0121450 A1* | 5/2014 | Kasic .................. H04R 25/60 600/25 |
| 2014/0121451 A1 | 5/2014 | Kasic et al. |
| 2014/0163308 A1 | 6/2014 | Miller et al. |
| 2014/0163309 A1 | 6/2014 | Bernhard et al. |
| 2014/0213139 A1 | 7/2014 | Ferguson |
| 2014/0242140 A1 | 8/2014 | Neu et al. |
| 2014/0257081 A1 | 9/2014 | Rapoport |
| 2014/0270297 A1 | 9/2014 | Gustafsson et al. |
| 2014/0275731 A1 | 9/2014 | Andersson et al. |
| 2014/0275736 A1 | 9/2014 | Ruppersberg et al. |
| 2014/0292321 A1 | 10/2014 | Yamazaki et al. |
| 2014/0293073 A1 | 10/2014 | Okamura et al. |
| 2014/0300437 A1 | 10/2014 | Fullerton et al. |
| 2014/0302741 A1 | 10/2014 | Whittaker |
| 2014/0321681 A1 | 10/2014 | Ball et al. |
| 2014/0336447 A1 | 11/2014 | Björn et al. |
| 2014/0343626 A1 | 11/2014 | Thenuwara et al. |
| 2014/0364681 A1 | 12/2014 | Hillbratt et al. |
| 2014/0364682 A1 | 12/2014 | Hillbratt et al. |
| 2014/0364922 A1 | 12/2014 | Garnham et al. |
| 2014/0375829 A1 | 12/2014 | Nishihara et al. |
| 2014/0379103 A1 | 12/2014 | Ishikawa et al. |
| 2015/0022298 A1 | 1/2015 | Fullerton |
| 2015/0032186 A1 | 1/2015 | Cushing et al. |
| 2015/0045607 A1 | 2/2015 | Håkansson |
| 2015/0045855 A1 | 2/2015 | Griffith |
| 2015/0087892 A1 | 3/2015 | Tourrel et al. |
| 2015/0092969 A1 | 4/2015 | Meskens et al. |
| 2015/0104052 A1 | 4/2015 | Gustafsson et al. |
| 2015/0117689 A1 | 4/2015 | Bergs et al. |
| 2015/0156595 A1 | 6/2015 | Zhong et al. |
| 2015/0157778 A1 | 6/2015 | Ishiyama et al. |
| 2015/0160426 A1 | 6/2015 | Chao et al. |
| 2015/0160470 A1 | 6/2015 | Terajima |
| 2015/0173468 A1 | 6/2015 | Stevenson |
| 2015/0192432 A1 | 7/2015 | Noguchi et al. |
| 2015/0201290 A1 | 7/2015 | Nikles et al. |
| 2015/0215708 A1 | 7/2015 | Meskens et al. |
| 2015/0265842 A1 | 9/2015 | Ridler et al. |
| 2015/0281860 A1 | 10/2015 | Johansson et al. |
| 2015/0312686 A1 | 10/2015 | Gustafsson et al. |
| 2015/0382114 A1 | 12/2015 | Andersson et al. |
| 2016/0021470 A1 | 1/2016 | Gustafsson |
| 2016/0037273 A1 | 2/2016 | Gustafsson |
| 2016/0058555 A1 | 3/2016 | Andersson et al. |
| 2016/0084920 A1 | 3/2016 | Liu et al. |
| 2016/0100260 A1 | 4/2016 | Ruppersberg et al. |
| 2016/0112813 A1 | 4/2016 | Hillbratt et al. |
| 2016/0161288 A1 | 6/2016 | Lu |
| 2016/0198270 A9 | 7/2016 | Nagl et al. |
| 2016/0205484 A1 | 7/2016 | Nagl et al. |
| 2016/0234613 A1 | 8/2016 | Westerkull |
| 2016/0247616 A1 | 8/2016 | Smith et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0078808 A1 | 3/2017 | Kennes |
| 2017/0111728 A1 | 4/2017 | Kim et al. |
| 2017/0162311 A1 | 6/2017 | Shmbo et al. |
| 2017/0162367 A1 | 6/2017 | Yokota et al. |
| 2017/0216523 A1 | 8/2017 | Neftel et al. |
| 2017/0251313 A1 | 8/2017 | Gustafsson |
| 2018/0160241 A1 | 6/2018 | Gustafsson et al. |
| 2018/0252228 A1 | 9/2018 | Henseler et al. |
| 2018/0270591 A1 | 9/2018 | Kennes |
| 2018/0288538 A1 | 10/2018 | Andersson et al. |
| 2018/0352349 A1 | 12/2018 | Fung et al. |
| 2018/0369586 A1 | 12/2018 | Lee et al. |
| 2019/0046797 A1 | 2/2019 | Calixto et al. |
| 2019/0076649 A1 | 3/2019 | Lee et al. |
| 2019/0151653 A1 | 5/2019 | Leigh et al. |
| 2019/0215623 A1 | 7/2019 | Bodvarsson |
| 2019/0239007 A1 | 8/2019 | Kennes et al. |
| 2019/0293454 A1 | 9/2019 | Bidaux et al. |
| 2020/0114151 A1 | 4/2020 | Smith et al. |
| 2020/0197702 A1 | 6/2020 | Eigentler |
| 2021/0046318 A1 | 2/2021 | Gibson et al. |
| 2021/0106815 A1 | 4/2021 | Smith et al. |
| 2021/0235209 A1 | 7/2021 | Kennes et al. |
| 2021/0257139 A1 | 8/2021 | Nellessen |
| 2021/0316136 A1 | 10/2021 | Smith et al. |
| 2022/0072302 A1 | 3/2022 | Zimmerling |

FOREIGN PATENT DOCUMENTS

| | | |
|---|---|---|
| EP | 2720480 A2 | 4/2014 |
| EP | 3307383 B1 | 3/2020 |
| GB | 414579 A | 8/1934 |
| GB | 2196855 A | 5/1988 |
| GB | 2205999 A | 12/1988 |
| GB | 2266045 A | 10/1993 |
| JP | 2010075394 A | 4/2010 |
| JP | 2012191448 A | 10/2012 |
| JP | 2013232860 A | 11/2013 |
| KR | 101743793 A | 5/2013 |
| KR | 101297828 B1 | 8/2013 |
| KR | 101537380 B1 | 7/2015 |
| WO | 9716835 A1 | 5/1997 |
| WO | 9939769 A1 | 8/1999 |
| WO | 2007024657 A1 | 3/2007 |
| WO | 2014008169 A1 | 1/2014 |
| WO | 2014011582 A2 | 1/2014 |
| WO | 2015065442 A2 | 5/2015 |
| WO | 2016207856 A1 | 12/2016 |
| WO | 2016207860 A1 | 12/2016 |
| WO | 2017046650 A1 | 3/2017 |
| WO | 2017105510 A1 | 6/2017 |
| WO | 2017105511 A1 | 6/2017 |
| WO | 2018200347 A1 | 11/2018 |
| WO | 2021059163 A1 | 4/2021 |

OTHER PUBLICATIONS

MED-EL, "FDA Hands MED-EL Approval for MRI Compatible Cochlear Implant (Video)," believed to be available in Jan. 2015.

* cited by examiner

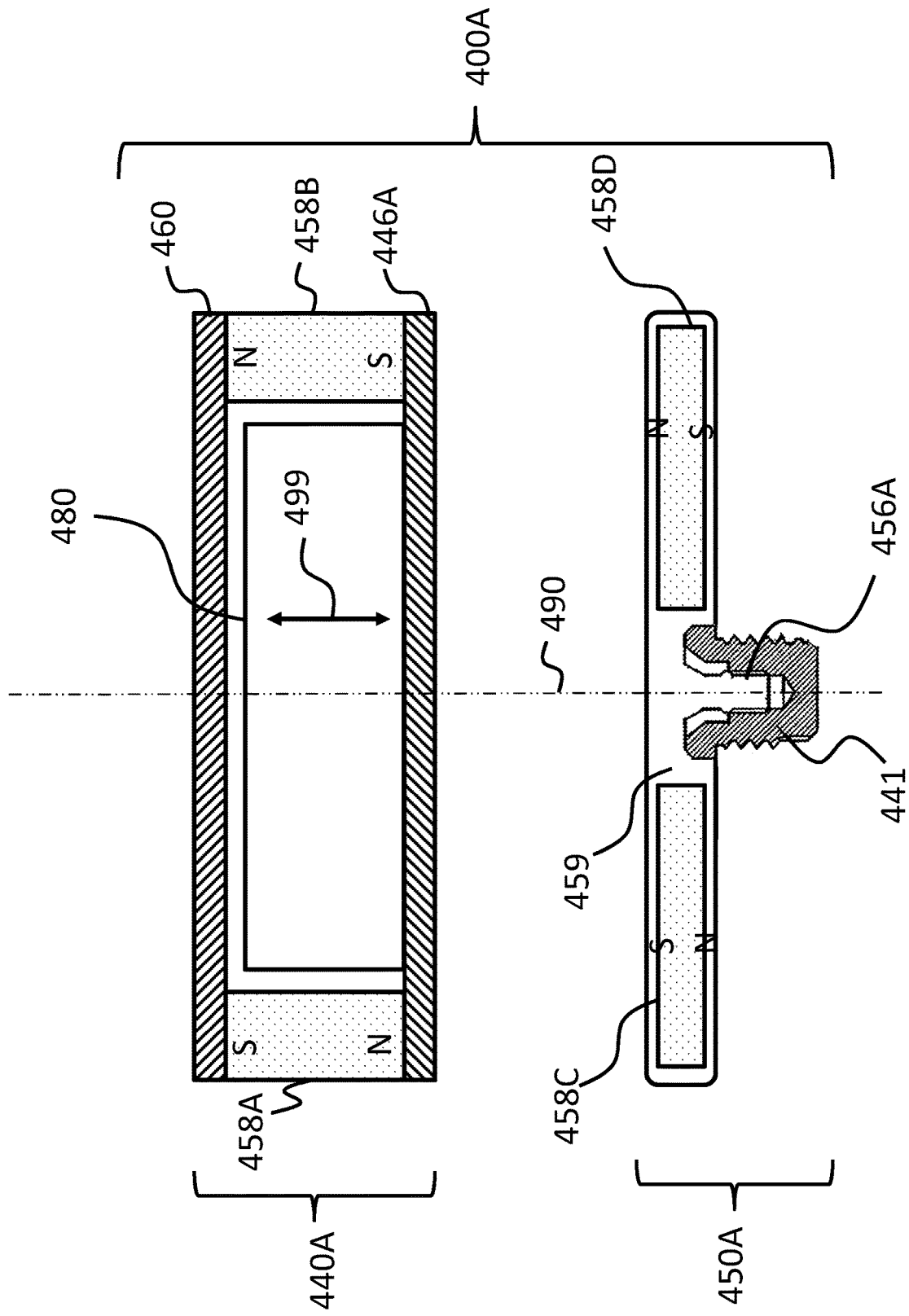

MAGNETIC RETENTION SYSTEM

CROSS-REFERENCE TO RELATED APPLICATIONS

This application is a Continuation application of U.S. patent application Ser. No. 17/387,551, filed Jul. 28, 2021, which is a Continuation application of U.S. patent application Ser. No. 16/148,146, filed Oct. 1, 2018, now U.S. Pat. No. 11,082,783, which is a Continuation application of U.S. patent application Ser. No. 14/811,138, filed Jul. 28, 2015, now U.S. Pat. No. 10,091,594, which claims priority to Provisional U.S. Patent Application No. 62/030,319, entitled BONE CONDUCTION MAGNETIC RETENTION SYSTEM, filed on Jul. 29, 2014, naming Johan GUSTAFSSON of Mölnlycke, Sweden, as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc., or for individuals who suffer from stuttering problems.

SUMMARY

In accordance with one aspect, there is an external component of a medical device, comprising a transducer including a static magnetic flux circuit that interacts with a dynamic magnetic flux circuit and a magnetic retention system configured to retain the external component to a recipient via interaction with a ferromagnetic component attached to a recipient, the magnetic retention system including a magnetic flux circuit that encircles the static magnetic flux path of the transducer.

In accordance with another aspect, there is an external component of a bone conduction system, comprising an actuator, and a permanent magnet separate from the actuator, wherein the permanent magnet generates a permanent magnetic field having substantial components located outside the actuator on substantially opposite sides of the actuator for removably attaching the external component to a recipient via interaction of the permanent magnetic field with ferromagnetic material of an implanted component.

In accordance with yet another aspect, there is a removable component of a bone conduction system, comprising a recipient interface component, an actuator coupled to the recipient interface component, the actuator including a seismic mass, wherein actuation of the actuator moves the seismic mass relative to the recipient interface component, and a plurality of retention magnets separate from the seismic mass.

BRIEF DESCRIPTION OF THE DRAWINGS

Some embodiments are described below with reference to the attached drawings, in which:

FIG. 4A is a schematic diagram of an exemplary embodiment of a bone conduction device;

DETAILED DESCRIPTION

Figure 1A:
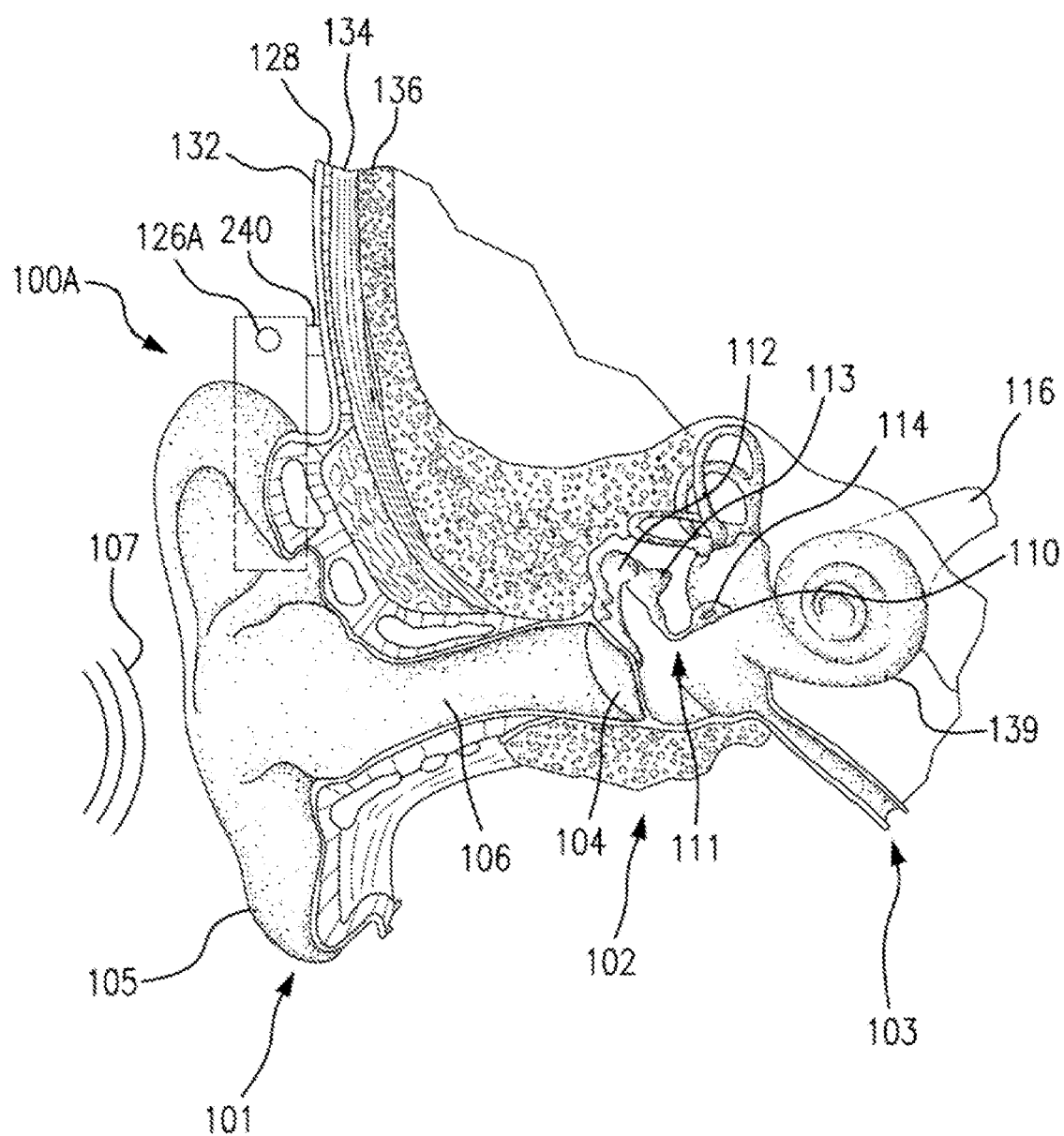
FIG. 1A is a perspective view of an exemplary bone conduction device in which at least some embodiments can be implemented.

FIG. 1A is a perspective view of a bone conduction device 100A in which embodiments may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 210 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1A also illustrates the positioning of bone conduction device 100A relative to outer ear 101, middle ear 102 and inner ear 103 of a recipient of device 100. As shown, bone conduction device 100 is positioned behind outer ear 101 of the recipient and comprises a sound input element 126A to receive sound signals. The sound input element may comprise, for example, a microphone, telecoil, etc. In an exemplary embodiment, sound input element 126A may be located, for example, on or in bone conduction device 100A, or on a cable extending from bone conduction device 100A.

In an exemplary embodiment, bone conduction device 100A comprises an operationally removable component and a bone conduction implant. The operationally removable component is operationally releasably coupled to the bone conduction implant. By operationally releasably coupled, it is meant that it is releasable in such a manner that the recipient can relatively easily attach and remove the operationally removable component during normal use of the bone conduction device 100A. Such releasable coupling is accomplished via a coupling assembly of the operationally removable component and a corresponding mating apparatus of the bone conduction implant, as will be detailed below. This as contrasted with how the bone conduction implant is attached to the skull, as will also be detailed below. The operationally removable component includes a sound processor (not shown), a vibrating electromagnetic actuator and/or a vibrating piezoelectric actuator and/or other type of actuator (not shown—which are sometimes referred to herein as a species of the genus vibrator) and/or various other operational components, such as sound input device 126A. In this regard, the operationally removable component is sometimes referred to herein as a vibrator unit. More particularly, sound input device 126A (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull.

As illustrated, the operationally removable component of the bone conduction device 100A further includes a coupling assembly 240 configured to operationally removably attach the operationally removable component to a bone conduction implant (also referred to as an anchor system and/or a fixation system) which is implanted in the recipient. In the embodiment of FIG. 1, coupling assembly 240 is coupled to the bone conduction implant (not shown) implanted in the recipient in a manner that is further detailed below with respect to exemplary embodiments of the bone conduction implant. Briefly, an exemplary bone conduction implant may include a percutaneous abutment attached to a bone fixture via a screw, the bone fixture being fixed to the recipient's skull bone 136. The abutment extends from the bone fixture which is screwed into bone 136, through muscle 134, fat 128 and skin 232 so that the coupling assembly may be attached thereto. Such a percutaneous abutment provides an attachment location for the coupling assembly that facilitates efficient transmission of mechanical force.

It is noted that while many of the details of the embodiments presented herein are described with respect to a percutaneous bone conduction device, some or all of the teachings disclosed herein may be utilized in transcutaneous bone conduction devices and/or other devices that utilize a vibrating electromagnetic actuator. For example, embodiments also include passive transcutaneous bone conduction systems where no active component (e.g., the actuator) is implanted beneath the skin (it is instead located in an external component), and the implantable part is, for instance, a ferromagnetic plate. Some embodiments of the passive transcutaneous bone conduction systems are configured for use where the vibrator (located in an external component) containing the actuator is held in place by pressing the vibrator against the skin of the recipient. In the embodiments detailed herein, the external component is held against the skin via a magnetic coupling (magnetic material and/or magnets being implanted in the recipient and the vibrator having a magnet and/or magnetic material to complete the magnetic circuit, thereby coupling the vibrator to the recipient).

Figure 1B:
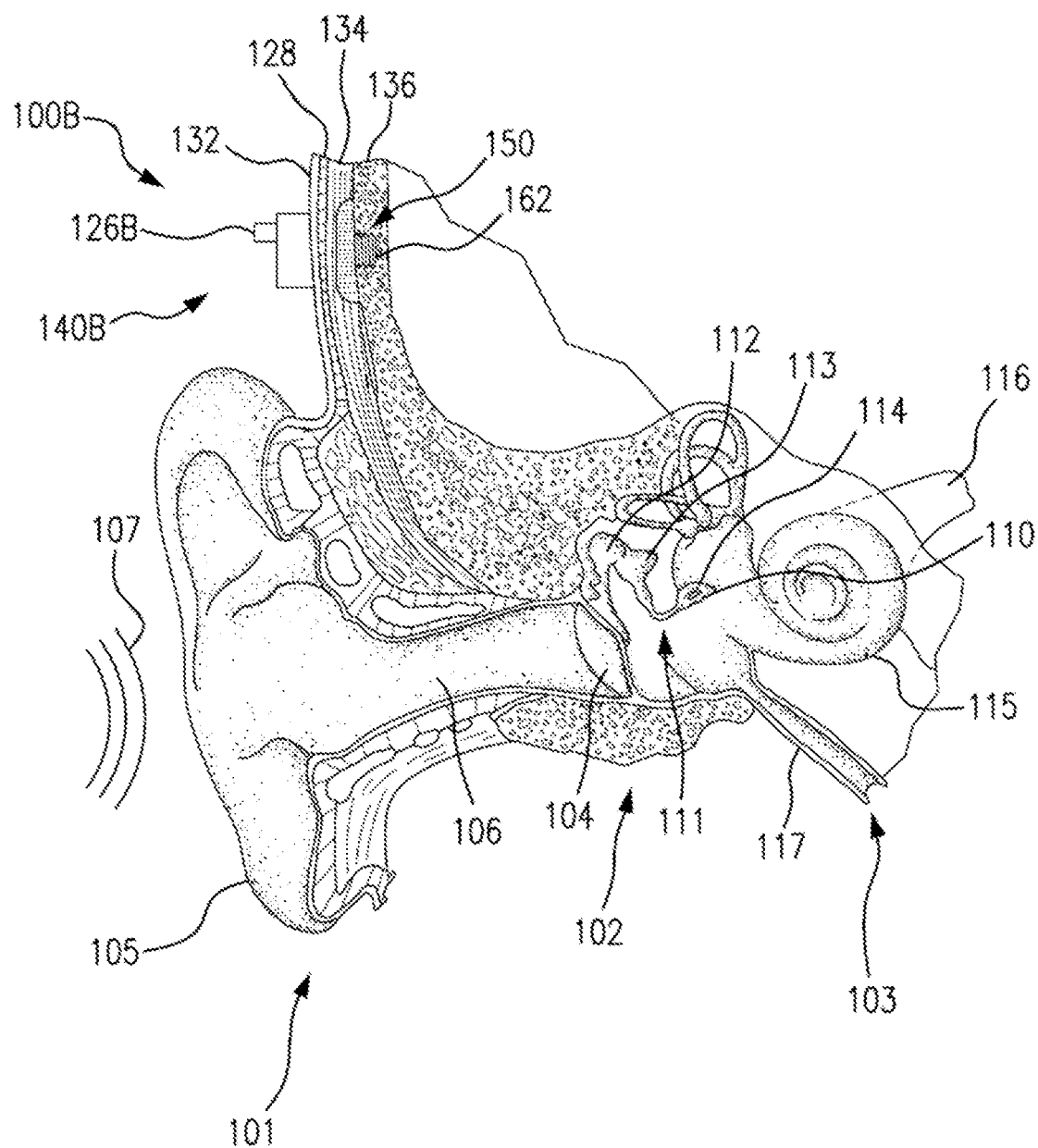
FIG. 1B is a perspective view of an alternate exemplary bone conduction device in which at least some embodiments can be implemented.

More specifically, FIG. 1B is a perspective view of a transcutaneous bone conduction device 100B in which embodiments can be implemented.

FIG. 1B also illustrates the positioning of bone conduction device 100B relative to outer ear 101, middle ear 102 and inner ear 103 of a recipient of device 100. As shown, bone conduction device 100 is positioned behind outer ear 101 of the recipient. Bone conduction device 100B comprises an external component 140B and implantable component 150. The bone conduction device 100B includes a sound input element 126B to receive sound signals. As with sound input element 126A, sound input element 126B may comprise, for example, a microphone, telecoil, etc. In an exemplary embodiment, sound input element 126B may be located, for example, on or in bone conduction device 100B, on a cable or tube extending from bone conduction device 100B, etc. Alternatively, sound input element 126B may be subcutaneously implanted in the recipient, or positioned in the recipient's ear. Sound input element 126B may also be a component that receives an electronic signal indicative of sound, such as, for example, from an external audio device. For example, sound input element 126B may receive a sound signal in the form of an electrical signal from an MP3 player electronically connected to sound input element 126B.

Bone conduction device 100B comprises a sound processor (not shown), an actuator (also not shown) and/or various other operational components. In operation, sound input device 126B converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with some embodiments, a fixation system 162 may be used to secure implantable component 150 to skull 136. As described below, fixation system 162 may be a bone screw fixed to skull 136, and also attached to implantable component 150.

In one arrangement of FIG. 1B, bone conduction device 100B can be a passive transcutaneous bone conduction device. That is, no active components, such as the actuator, are implanted beneath the recipient's skin 132. In such an arrangement, the active actuator is located in external component 140B, and implantable component 150 includes a magnetic plate, as will be discussed in greater detail below. The magnetic plate of the implantable component 150 vibrates in response to vibrations transmitted through the skin, mechanically and/or via a magnetic field, that are generated by an external magnetic plate.

Figure 2:
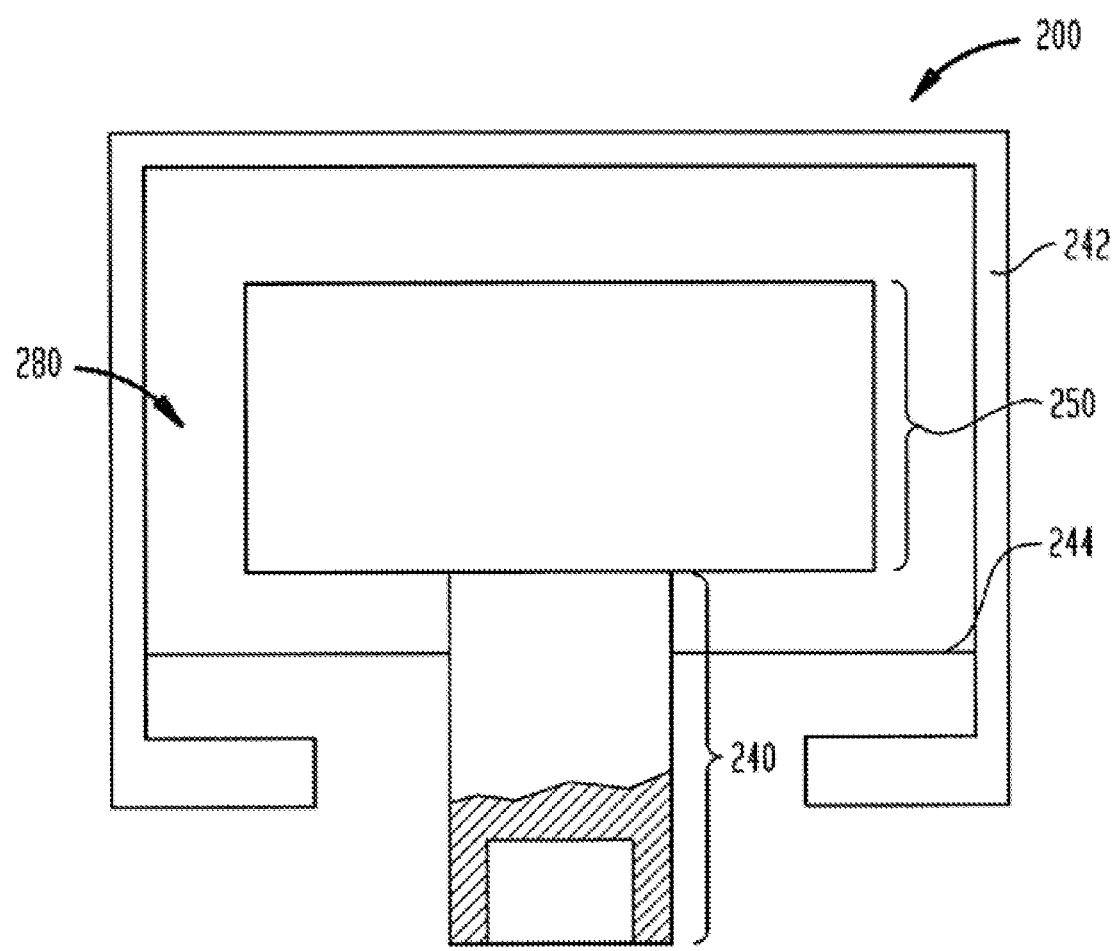
FIG. 2 is a schematic diagram conceptually illustrating a removable component of a percutaneous bone conduction device in accordance with at least some exemplary embodiments.

FIG. 2 is an embodiment of a removable component (external component) 200 of a bone conduction device in accordance with an embodiment corresponding to that of FIG. 1A, illustrating use of a percutaneous bone conduction device. Removable component 200, corresponding to, for example, the external component of bone conduction device 100A of FIG. 1A, includes a housing 242, a vibrating electromagnetic actuator 250, and a coupling assembly 240 that extends from housing 242 and is mechanically linked to vibrating electromagnetic actuator 250. Collectively, vibrating electromagnetic actuator 250 and coupling assembly 240 form a vibrating electromagnetic actuator-coupling assembly 280. Vibrating electromagnetic actuator-coupling assembly 280 is suspended in housing 242 by spring 244. In an exemplary embodiment, spring 244 is connected to coupling assembly 240, and vibrating electromagnetic actuator 250 is supported by coupling assembly 240. It is noted that while embodiments are detailed herein that utilize a spring, alternate embodiments can utilize other types of resilient elements. Accordingly, unless otherwise noted, disclosure of a spring herein also includes disclosure of any other type of resilient element that can be utilized to practice the respective embodiment and/or variations thereof.

Figure 3:
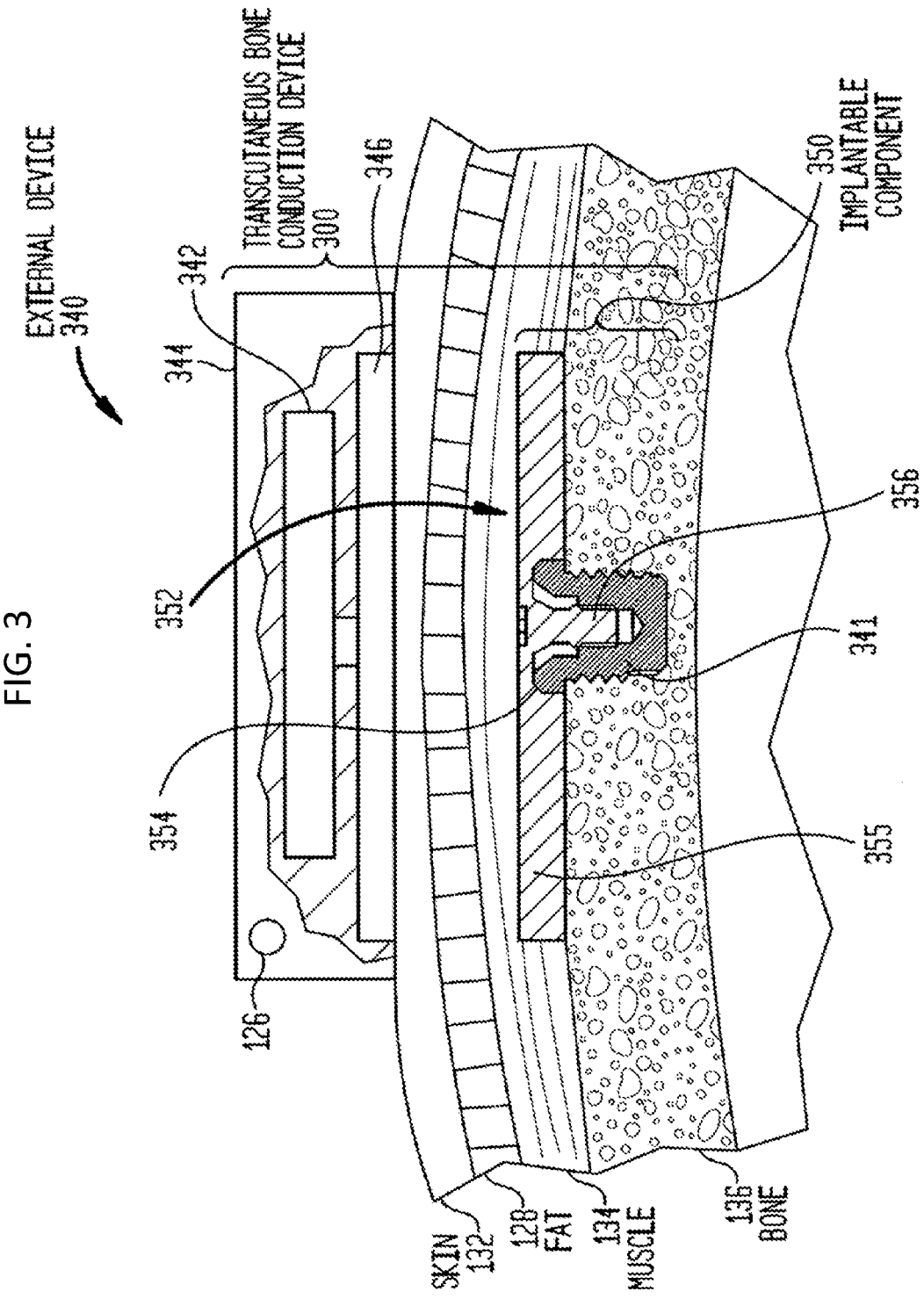
FIG. 3 is a schematic diagram conceptually illustrating a passive transcutaneous bone conduction device in accordance with at least some exemplary embodiments.

FIG. 3 depicts an exemplary embodiment of a transcutaneous bone conduction device 300 according to an embodiment that includes an external device 340 (corresponding to, for example, element 140B of FIG. 1B) and an implantable component 350 (corresponding to, for example, element 150 of FIG. 1B). The transcutaneous bone conduction device 300 of FIG. 3 is a passive transcutaneous bone conduction device in that a vibrating electromagnetic actuator 342 is located in the external device 340. Vibrating electromagnetic actuator 342 is located in housing 344 of the external component and is coupled to a support assembly in the form of a plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In an exemplary embodiment, the vibrating electromagnetic actuator 342 is a device that converts electrical signals into vibration. In operation, sound input element 126 converts sound into electrical signals. Specifically, the transcutaneous bone conduction device 300 provides these electrical signals to vibrating actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346, the vibrations are transferred from the vibrating actuator 342 to plate 346. Implanted plate assembly 352 is part of the implantable component 350, and is made of a ferromagnetic material that may be in the form of a permanent magnet that generates and/or is reactive to a magnetic field, or otherwise permits the establishment of a magnetic attraction between the external device 340 and the implantable component 350 sufficient to hold the external device 340 against the skin of the recipient, as will be detailed further below. Accordingly, vibrations produced by the vibrating electromagnetic actuator 342 of the external device 340 are transferred from plate 346 across the skin to plate 355 of implanted plate assembly 352. This can be accomplished as a result of mechanical conduction of the vibrations through the skin, resulting from the external device 340 being in direct contact with the skin and/or from the magnetic field between the two plates. These vibrations are transferred without penetrating the skin with a solid object, such as an abutment, as detailed herein with respect to a percutaneous bone conduction device.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw discussed in some additional detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

As will be detailed below, the teachings detailed herein and/or variations thereof can be applicable to the various embodiments of FIGS. 2-3 and/or variations thereof. In an exemplary embodiment, the various teachings detailed herein and/or variations thereof can be applied to the various embodiments of FIGS. 2-3 to obtain a hearing prosthesis where a vibrating actuator of an external component (element 200 of FIG. 2, element 340 of FIG. 3) is removably attached to a recipient such that the actuator is in vibrational communication with a recipient such that vibrations generated by the vibrating electromagnetic actuator in response to a sound captured by sound capture devices of the various embodiments are ultimately transmitted to bone of a recipient in a manner that at least effectively evokes hearing percept. By "effectively evokes a hearing percept," it is meant that the vibrations are such that a typical human between 18 years old and 40 years old having a fully functioning cochlea that receives such vibrations, where the vibrations communicate speech, would be able to understand the speech communicated by those vibrations in a manner sufficient to carry on a conversation provided that those adult humans are fluent in the language forming the basis of the speech. That said, it is noted that embodiments can also effectively evoke a hearing percept in humans younger than 18 years old and older than 40 years old and/or in humans without a fully functioning cochlea and/or in humans that are not completely fluent in the language forming the basis of the speech. In other words, the aforementioned population of 18 to 40 year olds is provided by way of example and not by way of limitation.

Some exemplary features of a magnetic retention system for retaining the removable external device of a bone conduction device to a recipient will now be described in terms of a passive transcutaneous bone conduction device of FIG. 1B, followed by an example of use for a percutaneous bone conduction device of FIG. 1A. It is noted that any and/or all of these features and/or variations thereof may be utilized in other types of prostheses and/or medical devices and/or other devices. It is further noted that while embodiments detailed herein are often referred to in terms of the electromagnetic transducer being an actuator, it is to be understood that any of these teachings, unless otherwise specifically noted, are equally applicable to electromagnetic transducers that receive vibration and output a signal resulting from the received vibrations. It is further noted that other types of actuators, such as by way of example only and not by way of limitation, piezoelectric actuators, can be utilized in some embodiments. That is, any disclosure detailed herein of an electromagnetic actuator/transducer corresponds to a disclosure of a piezoelectric actuator/transducer.

More specifically, referring now to FIG. 4A, which depicts a schematic of an exemplary bone conduction device 400A, the exemplary bone conduction device 400A utilizing permanent magnets to retain external device 440A corresponding to external device 340 of FIG. 3. FIG. 4A further depicts an implantable component 450A corresponding to implantable component 350 of FIG. 3.

In an exemplary embodiment, external device 440A has the functionality of a transducer/actuator, irrespective of whether it is used with implantable component 450A. That is, in some exemplary embodiments, external device 440A will vibrate whether or not the implantable component 450A is present (e.g., whether or not the static magnetic field extends to the implantable component 450A, as will be detailed below).

The external device 440A includes a vibrating electromagnetic actuator enclosed in a housing, hereinafter referred to as an actuator assembly, represented by black box 480. Additional details of the vibrating electromagnetic actuator are provided below. Again it is noted that in an alternate embodiment, black box 480 is an actuator assembly that is a piezoelectric actuator.

External device 440A further includes element 458A, which is a permanent magnet having a North-South alignment in a first direction relative to a longitudinal axis 490 of the electromagnetic actuator (the vertical direction of FIG. 4A, which is parallel to the direction of movement of components of the actuator during actuation thereof, indicated by arrow 499, as will be detailed below). Element 458B is a permanent magnet having a North-South alignment in a second direction relative to a longitudinal axis of the electromagnetic actuator, the second direction being opposite the first direction. In an exemplary embodiment, the permanent magnets are bar magnets (having a longitudinal direction extending normal to the plane of FIG. 4A). In some embodiments, the bar magnets have hogged-out sections in the center to accommodate the actuator assembly 480. In some embodiments, the magnets can be "C" shaped magnets, with the tips of the "C" facing the opposite "C." In some embodiments, the magnets can be crescent moon magnets. In alternative embodiments, other configurations of the magnets can be utilized. It is noted that in some embodiments, the shapes of the permanent magnets of the implantable components may drive the shapes of the magnets of the external component. For example, if magnets of the implantable component are half-moon shaped (collectively forming a circular shape), the permanent magnets of the external component can be semi-circular shaped and/or half-circular shaped (all shapes with respect to the cross-section lying on a plane normal to the longitudinal axis of the bone conduction device). Any configuration of permanent magnet(s) that can enable the teachings detailed herein and/or variations thereof to be practiced can be utilized in at least some embodiments.

FIG. 4A also shows that external device 440A includes a support assembly 446A, which corresponds to plate 346 of FIG. 3 as described above. It is through support assembly 446A that vibrations generated by the actuator of actuator assembly 480 of the external device 440A are transferred from the external component 440A to the skin of the recipient to evoke a hearing percept. In an exemplary embodiment, support assembly 446A is made at least partially of a non-ferromagnetic material that is compatible with the skin of the recipient (or at least is coated with a material that is compatible with the skin of the recipient). In at least some exemplary embodiments, the support assembly 446A is free of any permanent magnet components. In this regard, in at least some exemplary embodiments, the support assembly 446A is configured to substantially avoid influencing the magnetic flux generated by the permanent magnets 458A and 458B.

It is noted that in an exemplary embodiment, the external device 440A can be located within a housing. In an exemplary embodiment, the housing can be a housing that is connected to the components depicted in FIG. 4A by a spring. Alternatively, the housing can be rigidly mounted to the components depicted in FIG. 4A.

Continuing with reference to FIG. 4A, the device 400A further includes an implantable component 450A, corresponding to implantable component 350 of FIG. 3. In some embodiments, implantable component 450A includes at least two permanent magnets 458C and 458D. Permanent magnet 458C has a North-South alignment in a first direction relative to a longitudinal axis of the electromagnetic actuator (the vertical direction of FIG. 4A). Permanent magnet 458D has a North-South alignment in a second direction relative to a longitudinal axis of the electromagnetic actuator, the second direction being opposite the first direction. In an exemplary embodiment, the permanent magnets are bar magnets (having a longitudinal direction extending normal to the plane of FIG. 4A). In at least some exemplary embodiments, during operational use of the bone conduction device 400A, the external device 440A is aligned with the implantable component 450A such that the poles of the permanent magnets 458A and 458C have a North-South alignment in the same direction and the poles of the permanent magnets 458B and 458D have a North-South alignment in the same direction (but opposite of that of magnets 458A and 458C). In at least some exemplary embodiments, permanent magnets 458C and 458D are bar magnets connected to one another via chassis 459 of the implantable component 450A. In an exemplary embodiment, the chassis 459 is a nonmagnetic material (e.g., titanium). In alternative embodiments, other configurations of the magnets can be utilized, some of which will be described below. Any configuration of permanent magnet(s) that can enable the teachings detailed herein and/or variations thereof to be practiced can be utilized in at least some embodiments.

That said, in an alternative embodiment, it is noted that the implantable component 450A does not include permanent magnets. In at least some embodiments, elements 458C and 458D are replaced with other types of ferromagnetic material (e.g. soft iron (albeit encapsulated in titanium, etc.)). Also, elements 458C and 458D can be replaced with a single, monolithic component. Any configuration of ferromagnetic material of the implantable component 450A that will enable the permanent magnets of the external device 440A to establish a magnetic coupling with the implantable component 450A that will enable the external device 440A to be retained on the surface of the skin as detailed herein can be utilized in at least some embodiments.

In operation, sound input element 126 (FIG. 3) converts sound into electrical signals. As noted above, the bone conduction device provides these electrical signals to a sound processor which processes the signals and provides the processed signals to the vibrating electromagnetic actuator of external device 440A, which then converts the electrical signals (processed or unprocessed) into vibrations. Because the vibrating electromagnetic actuator of external device 440A is mechanically coupled to support assembly 446A, which can include a plate having a surface configured to abut skin of the recipient, the vibrations are transferred from the vibrating electromagnetic actuator to support assembly 446A and then to the recipient via the support assembly 446A, to evoke a hearing percept, all while the external device 440A is retained on the recipient via the magnetic coupling between the permanent magnets of the external device 440A and the ferromagnetic material (e.g., permanent magnets) of the implantable component 450A.

Figure 4B:
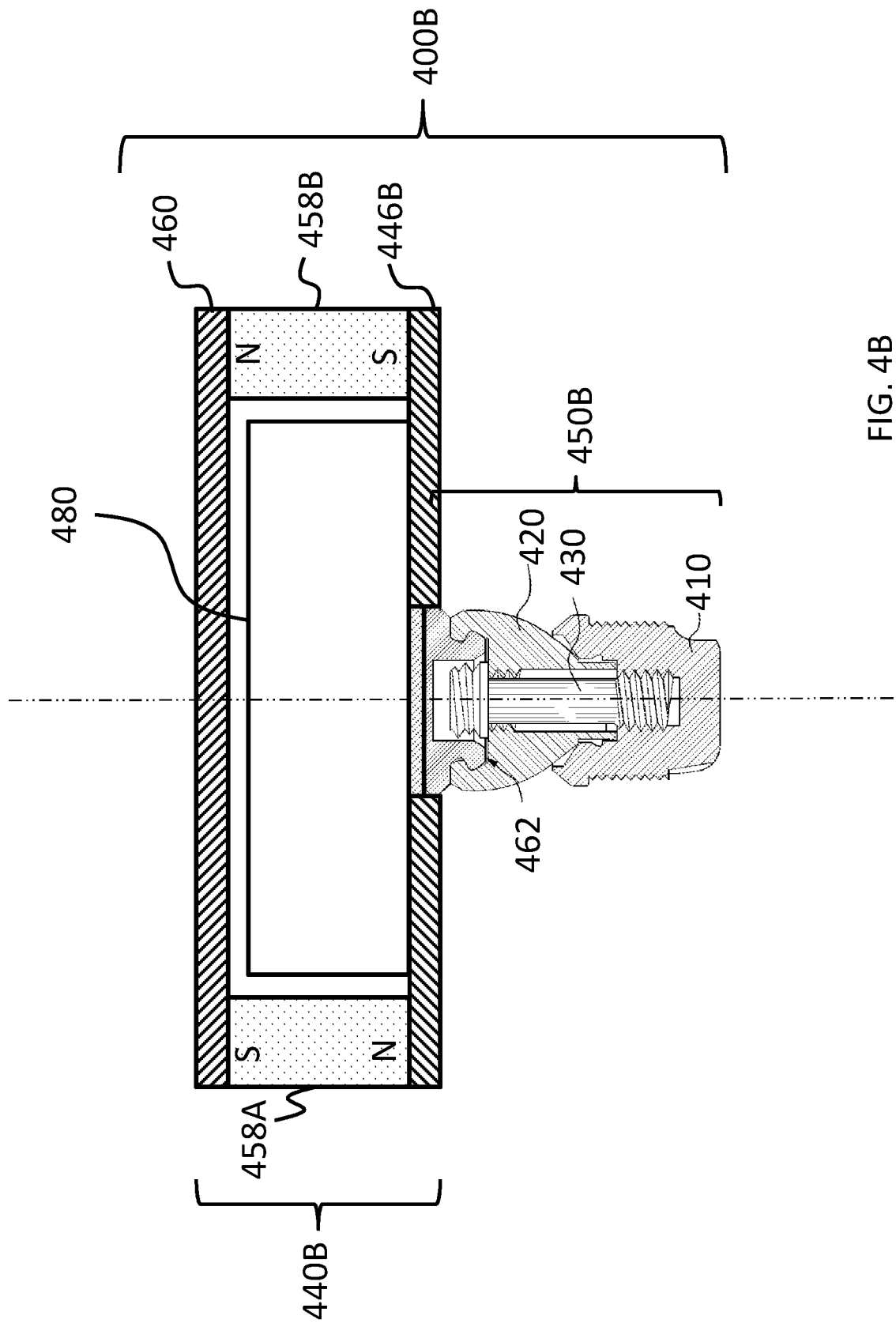
FIG. 4B is a schematic diagram of another exemplary embodiment of a bone conduction device.

As noted above, in some embodiments some of the teachings detailed herein are applicable to percutaneous bone conduction devices. FIG. 4B depicts a schematic of an exemplary bone conduction device 400B corresponding to the removable external component of the bone conduction device 200 of FIG. 2 plus an implantable component 450B, the exemplary bone conduction device 400B having the aforementioned static magnetic flux features.

In an exemplary embodiment, external device 440B has the functionality of a transducer/actuator, irrespective of whether it is used with implantable component 450B. The external device 440B includes an actuator assembly, again represented by black box 480. External device 440B further includes the permanent magnets and the yoke (the latter being optional) of FIG. 4A.

The external device 440B further includes a support assembly 446B. When the actuator of the actuator assembly 480 is actuated, a counterweight assembly of the actuator (also referred to as seismic mass, discussed in greater detail below) moves relative to the support assembly, as will be further detailed below, and thus generates vibrations, which are transmitted through the support assembly 446B.

Support assembly 446B is configured to interface with a cap 462 of implantable component 450B, and thus support assembly 446B is a recipient interface component. Specifically, support assembly 446B includes a recess configured to receive cap 462. In the embodiment of FIG. 4B, the external device 440B (the removable component) is held to the implantable component 450B in general, or to the cap 462 in particular, via magnetic attraction due to the permanent magnets 458A and 458B, as cap 460 includes a ferromagnetic component (e.g., soft iron and/or permanent magnets), as will be described below. First, however, additional details of the implantable component 450B will now be described.

Specifically, implantable component 450B of FIG. 4B is in the form of bone conduction implant which includes a percutaneous abutment attached to a bone fixture via a screw, the bone fixture being fixed to the recipient's skull bone 136. The abutment extends from the bone fixture which is screwed into bone 136, through muscle 134, fat 128 and skin 132 so that the coupling apparatus can be attached thereto. Such a percutaneous abutment provides an attachment location for the coupling apparatus of the removable component of the percutaneous bone conduction device that facilitates efficient transmission of mechanical force from the removable component 440B to the implantable component 450B. More specifically, the implantable component 450B includes a bone fixture 410 configured to screw into the skull bone 136, a skin-penetrating abutment 420 and an abutment screw 430 that is in the form of an elongate coupling shaft. As may be seen, the abutment screw 430 connects and holds the abutment 420 to the fixture 410, thereby rigidly attaching abutment 420 to bone fixture 410. The rigid attachment is such that the abutment is vibrationally connected to the fixture 410 such that at least some of the vibrational energy transmitted to the abutment is transmitted to the fixture in a sufficient manner to effectively evoke a hearing percept.

As noted above, bone conduction implant 450B further includes a cap 462, which is or includes a ferromagnetic component, although in alternate embodiments, a ferromagnetic component is part of the abutment 420 (in which case the cap may or may not be present). The cap 462 is directly attached to the abutment 420 via a snap-couple, although in other embodiments, it can be connected in another manner (e.g., screwed onto the abutment screw 430, welded or otherwise adhered to the abutment, etc.). Any device, system or method that will enable the implantable component 450B to serve as a component that will enable the removable component 440B to be magnetically coupled thereto can be used in some embodiments.

While the configuration depicted in FIG. 4B depicts the implantable component 450B having a male configuration that is received in the female configuration of the removable external component 440B, the reverse can be the case in some embodiments. Any configuration that will enable the removable external component 440B to be magnetically held to the implantable component 450B can be used in some embodiments providing that the teachings detailed herein and/or variations thereof can be practiced.

Prior to describing some specifics of the performance of the magnetic retention system according to some embodiments, some high-level principles of operation of an exemplary electromagnetic actuator of the actuator assembly 480 will now be described. It is noted that these are but exemplary features of an exemplary electromagnetic actuator, and other actuators can be used in alternate embodiments. For example, the actuator described below is a "balanced actuator." Conversely, an unbalanced actuator can be used. Further, as noted above, a piezoelectric actuator can be used. The following provides a frame of reference to describe the circuit of the magnetic flux of the retention system relative to the magnetic flux circuits of the of the electromagnetic actuator of the actuator assembly 480 (in embodiments that so use an electromagnetic actuator).

Figure 5:
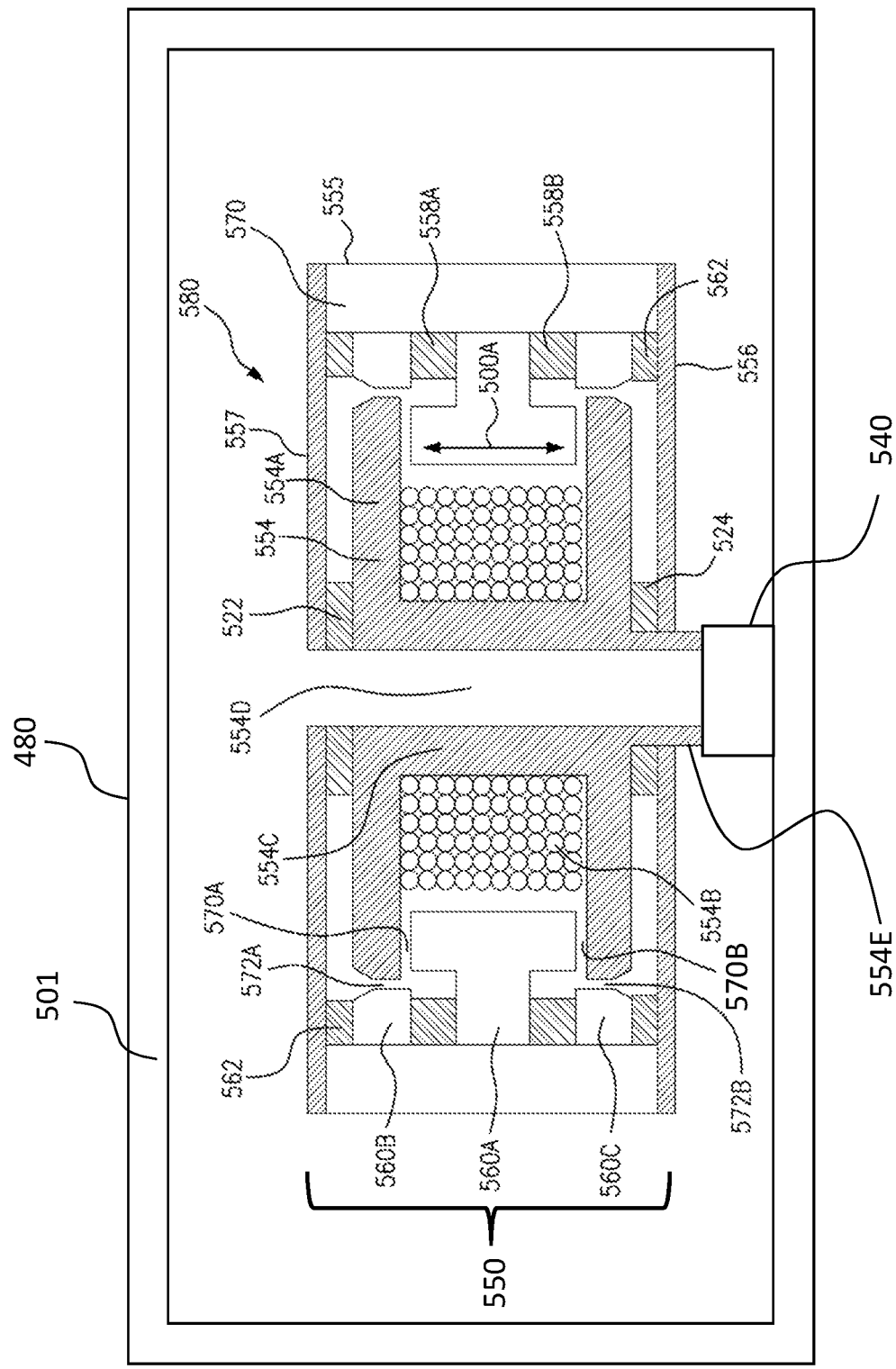
FIG. 5 is a schematic diagram of an exemplary electromagnetic actuator assembly according to an exemplary embodiment.

FIG. 5 is a cross-sectional view of the actuator assembly 480 used in the embodiments of FIGS. 4A and 4B. The actuator assembly 480 includes a housing 501 that encloses a vibrating electromagnetic actuator-coupling assembly 580.

The vibrating electromagnetic actuator-coupling assembly 580 includes a vibrating electromagnetic transducer 550 in the form of an actuator and a vibration transfer component 540. Vibration transfer component 540 is rigidly connected to vibrating electromagnetic transducer 550 and transfers vibrational energy therefrom to the housing 501 (although in other embodiments, vibration transfer component 540 is configured to conduct the vibrations through the housing 501) and thus to the support apparatuses of the various devices (446A, 446B) so that it can be transferred to the recipient to evoke a hearing percept.

As illustrated in FIG. 5, vibrating electromagnetic actuator 550 includes a bobbin assembly 554 and a counterweight assembly 555 (also referred to as a seismic mass). As illustrated, bobbin assembly 554 includes a bobbin 554A and a coil 554B that is wrapped around a core 554C of bobbin 554A. In the illustrated embodiment, bobbin assembly 554 is radially symmetrical. It is noted that unless otherwise specified, the electromagnetic transducers detailed herein are radially symmetrical.

Counterweight assembly 555 includes springs 556 and 557, permanent magnets 558A and 558B, yokes 560A, 560B and 560C, spacers 562, and counterweight mass 570. Spacers 562 provide a connective support between spring 556 and the other elements of counterweight assembly 555 just detailed, although it is noted that in some embodiments these spacers are not present and the spring is connected only to the counterweight mass 570, while in other embodiments the spring is only connected to the spacers. Springs 556 and 557 connect bobbin assembly 554 via spacers 522 and 524 to the rest of counterweight assembly 555 and permit counterweight assembly 555 to move relative to bobbin assembly 554 upon interaction of a dynamic magnetic flux produced by coil 554B. The static magnetic flux is produced by permanent magnets 558A and 558B of counterweight assembly 555. In this regard, counterweight assembly 555 is a static magnetic field generator where the permanent magnets 558A and 558B are arranged such that their respective south poles face each other and their respective north poles face away from each other. It is noted that in other embodiments, the respective south poles may face away from each other and the respective north poles may face each other.

Coil 554B, in particular, may be energized with an alternating current to create the dynamic magnetic flux about coil 554B. In an exemplary embodiment, bobbin 554A is made of a soft iron. The iron of bobbin 554A is conducive to the establishment of a magnetic conduction path for the dynamic magnetic flux. In an exemplary embodiment, the yokes of the counterweight assembly 555 are made of soft iron also conducive to the establishment of a magnetic conduction path for the static magnetic flux.

The soft iron of the bobbin and yokes may be of a type that increases the magnetic coupling of the respective magnetic fields, thereby providing a magnetic conduction path for the respective magnetic fields. As will be further detailed below, in other embodiments, other types of material, at least for the bobbin, can be utilized in at least some embodiments.

As may be seen, vibrating electromagnetic actuator 550 includes two axial air gaps 570A and 570B that are located between bobbin assembly 554 and counterweight assembly 555. With respect to a radially symmetrical bobbin assembly 554 and counterweight assembly 555, such as that detailed in FIG. 5, air gaps 570A and 570B extend in the direction of the primary relative movement between bobbin assembly 554 and counterweight assembly 555, indicated by arrow 500A (the primary relative movement is discussed in greater detail below).

Further, as may be seen in FIG. 5, the vibrating electromagnetic actuator 550 includes two radial air gaps 572A and 572B that are located between bobbin assembly 554 and counterweight assembly 555. With respect to a radially symmetrical bobbin assembly 554 and counterweight assembly 555, the air gap extends about the direction of relative movement between bobbin assembly 554 and counterweight assembly 555. As may be seen in FIG. 5, the permanent magnets 558A and 558B are arranged such that their respective south poles face each other and their respective north poles face away from each other.

In the electromagnetic actuator of FIG. 5, the radial air gaps 572A and 572B close static magnetic flux between the bobbin 554A and the yokes 560B and 560C, respectively. Further, axial air gaps 570A and 570B close the static and dynamic magnetic flux between the bobbin 554A and the yoke 560A. Accordingly, in the radially symmetrical device of FIG. 5, there are a total of four (4) air gaps. In an exemplary embodiment, the air gaps are gaps in which little to no material having substantial magnetic aspects is located in the air gap. They are areas of relatively high reluctance but magnetic flux still flows therethrough. Accordingly, an air gap is not limited to a gap that is filled by air. In this vein, additional gaps that do not close a magnetic field may be present, but they are not air gaps.

Is further noted that while the exemplary embodiments depicted in the figures correspond to a balance electromagnetic actuator (transducer) alternate embodiments can utilize unbalanced electromagnetic actuators. Any type of actuator (transducer) that can be utilized to implement the teachings detailed herein and are variations thereof can utilize in at least some embodiments.

As can be seen from FIG. 5, the vibrating electromagnetic actuator 550 includes a passage passing all the way therethrough. (In order to better convey the concepts of the teachings herein, the "background lines" of the cross-sectional views are not depicted in the figures.) It is to be understood that in at least the case of a radially symmetric transducer according to the embodiment of FIG. 5, components such as springs 556 and 557, the bobbin 664, etc., extend about the longitudinal axis of the transducer. (It was determined that depicting such background lines would distract from the concepts of the teachings herein.) More particularly, the bobbin 554A includes space therein, in the form of bore 554D that passes all the way therethough, including through bobbin extension 554E.

The arrangement of the permanent magnets 458A and 458B relative to the actuator of actuator assembly 480 can have some exemplary utilitarian value as will be partially described below. With respect to the arrangement, in view of the above, it can be seen that in some embodiments, there is a removable component of a bone conduction system, such as by way of example and not by way of limitation, external components 440A and 440B of bone conduction devices 400A and 400B as detailed in FIGS. 4A and 4B, where the removable components 440A and 400B can comprise a recipient interface component, such as by way of example only and not by way of limitation, support assembly 446A and 446B as detailed above. The removable component further includes an actuator coupled to the recipient interface component, the actuator including a seismic mass. Accordingly, in an exemplary embodiment, the actuator can correspond to the actuator of the actuator assembly 480 detailed above. In this exemplary embodiment, actuation of the actuator moves the seismic mass relative to the recipient interface component. In an exemplary embodiment, this is achieved by rigidly fastening the actuator assembly 480 to the recipient interface/support assembly 446A or 446B. The removable component further includes a plurality of retention magnets 458A and 458B separate from the seismic mass.

The arrangement of FIGS. 4A and 4B in view of FIG. 5 can be described as an external component 440A that is configured such that actuation of the actuator of the actuator assembly 480 moves a seismic mass (counterweight assembly 555) along a first direction (e.g., as represented by arrows 499 of FIG. 4A and 500A of FIG. 5) normal to a surface of skin of a recipient of the device. The magnetic retention system of the external component includes at least one permanent magnet (one or both of permanent magnets 458A and 458B). The actuator of the external component includes at least one permanent magnet 558A and/or 558B. A plane normal to the first direction (represented by plane 691 of FIG. 6, discussed below) bisects at least one permanent magnet of the actuator (558A and/or 558B) and the at least one permanent magnet of the magnetic retention system (458A and/or 458B).

As can be seen from the embodiments of FIGS. 4A and 4B, which are symmetric about the plane normal to the view thereof, the actuator (e.g., actuator 550, located within housing 501 of the actuator assembly 480) is located between the permanent magnets 458A and 458B. In an exemplary embodiment, this enables the removable component to have an overall height that is less than that which would be the case if the permanent magnets were located between the actuator and the implantable component (450A or 450B).

It is noted that during operation of the bone conduction devices detailed herein, there will be some movement of the overall removable component 440A or 440B. By way of example only and not by way of limitation, with respect to the passive transcutaneous bone conduction system, where the skin supports the removable component 440A, actuation of the actuator thereof will cause the entire removable component 440A to move back and forth towards and away from the underlying bone, owing to the flexibility of the overlying skin. However, a magnitude of movement of the seismic mass of the actuator is greater than that of any movement of the retention magnets 458A and 458B, relative to bone of the recipient adjacent to the external component and/or relative to the recipient interface component 446A. With regard to the latter, in a perfect system, the retention magnets 458A and 458B will not move relative to the support assembly 446A. Because all systems are not perfect, there will be some movement. However, the magnitude of that movement will be much lower than that of the seismic mass.

Figure 6:
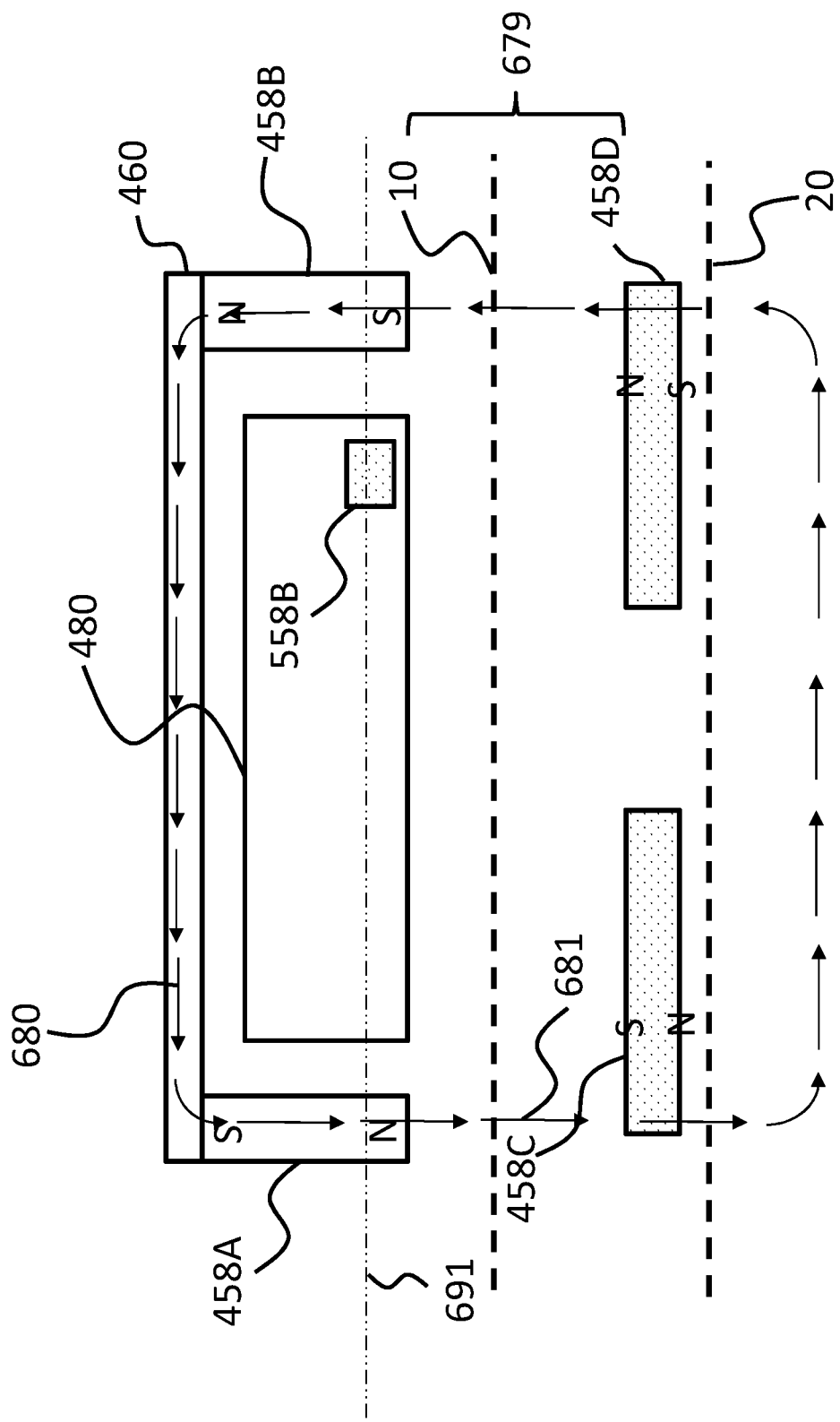
FIG. 6 is a schematic diagram of an exemplary magnetic flux circuit of a retention system according to an exemplary embodiment.

FIG. 6 depicts an exemplary static magnetic flux generated by the permanent magnets 458A and 458B, along with the permanent magnets 458C and 458D, used to retain the external component 440A to the recipient (FIG. 6 corresponds to the embodiment of FIG. 4A, with some components of the bone conduction device are removed for clarity). Again it is noted that in some embodiments, a different implantable component arrangement can be used (having different permanent magnets that that depicted, or none, as will be detailed below). As can be seen from FIG. 6, the static magnetic flux 680 travels in a circuit 681 that crosses the outer surfaces of the skin 132 (represented by dashed line 10), fat 128 and muscle 134 layers of the recipient. The distance between the permanent magnets 458A and 458B and the implantable component constituting an air gap 679 (providing that no magnetically conductive components/components having magnetic attributes are located therebetween—if so, the air gap distance would be different). The static magnetic flux circuit 681 also crosses the outer surface of bone 136 (represented by dashed line 20). Accordingly, the plurality of retention magnets 448A and 448B generate a magnetic field having a single (i.e., only one) magnetic retention circuit 681. That said, there may be multiple circuits, but the circuits will be aligned relative to a frame of reference of FIG. 6 (there can be more circuits "in front of" and/or "behind" that depicted in FIG. 6 (e.g., due to the use of multiple bar magnets in front of and/or behind that depicted in FIG. 6)). It is noted that the retention magnets can generate a flux having another circuit, but if that circuit is not a retention circuit (i.e., used to retain the removable component to the recipient), there is still only one retention circuit.

Also as can be seen from FIG. 6, the static magnetic flux is asymmetrical. In an exemplary embodiment, the static magnetic flux 680 flows in one direction in one circuit (circuit 681), and there is not another static magnetic flux circuit that flows in an opposite direction, or at least not a direction that would render the static magnetic flux (overall static magnetic flux of the bone conduction device) to be symmetrical. Further, as can be seen from FIG. 6, the external component 440A is configured such that the static magnetic flux flows in a circuit (circuit 681) that flows through the two permanent magnets 458A and 458B and at least one yoke (yoke 460) that is a part of the external component. A substantial portion of the static magnetic flux 680 that flows in the circuit 681 flows through at least one of an implantable permanent magnet (458C and/or 458D) or a second yoke (where permanent magnets 458C and 458D of the figures is replaced with a ferromagnetic material such as soft iron etc., as noted above) that is implantable.

Figure 7:
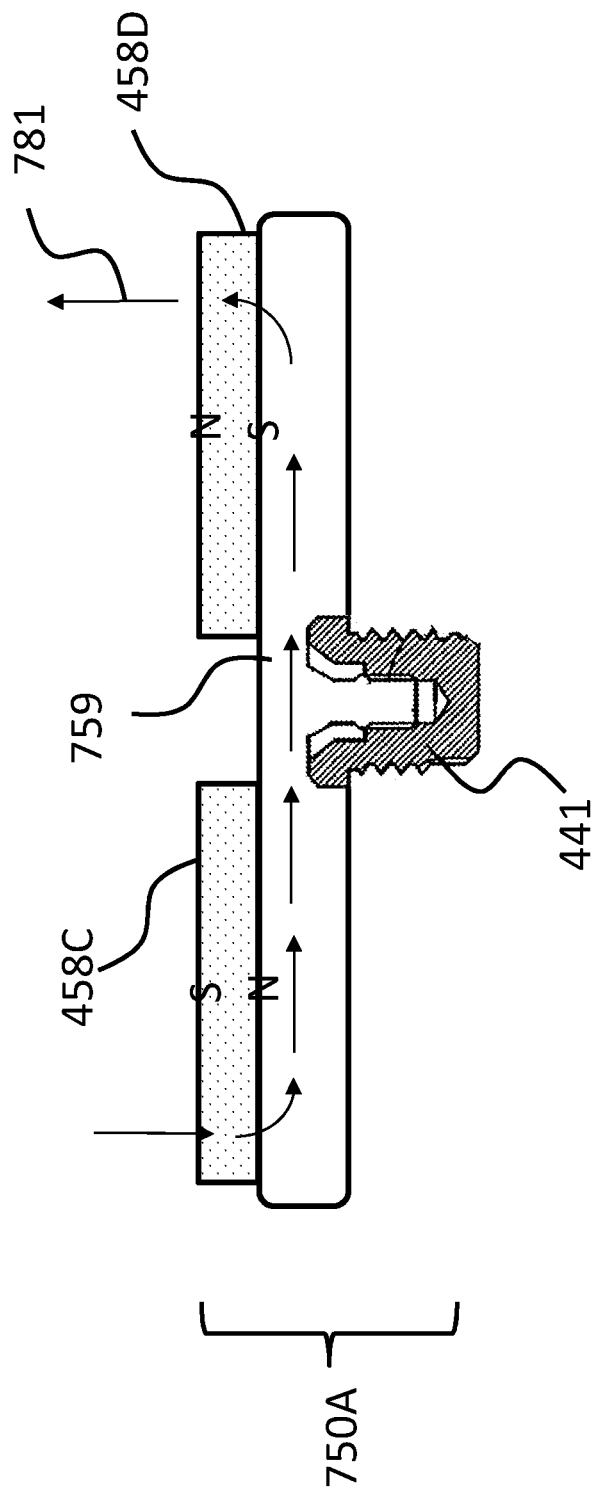
FIG. 7 is a schematic diagram of a portion of another exemplary magnetic flux circuit of a retention system according to an exemplary embodiment.

That said, FIG. 7 depicts an alternate embodiment of an implantable component, implantable component 750A, which includes a yoke 759 to which the permanent magnets 458C and 458D are attached. FIG. 7 depicts a portion of a flux circuit 781, which is identical to that of flux circuit 681 of FIG. 6, except that the flux travelling between magnet 458C and 458D is channeled through yoke 759. In an exemplary embodiment, yoke 759 is a soft iron component.

Figure 8:
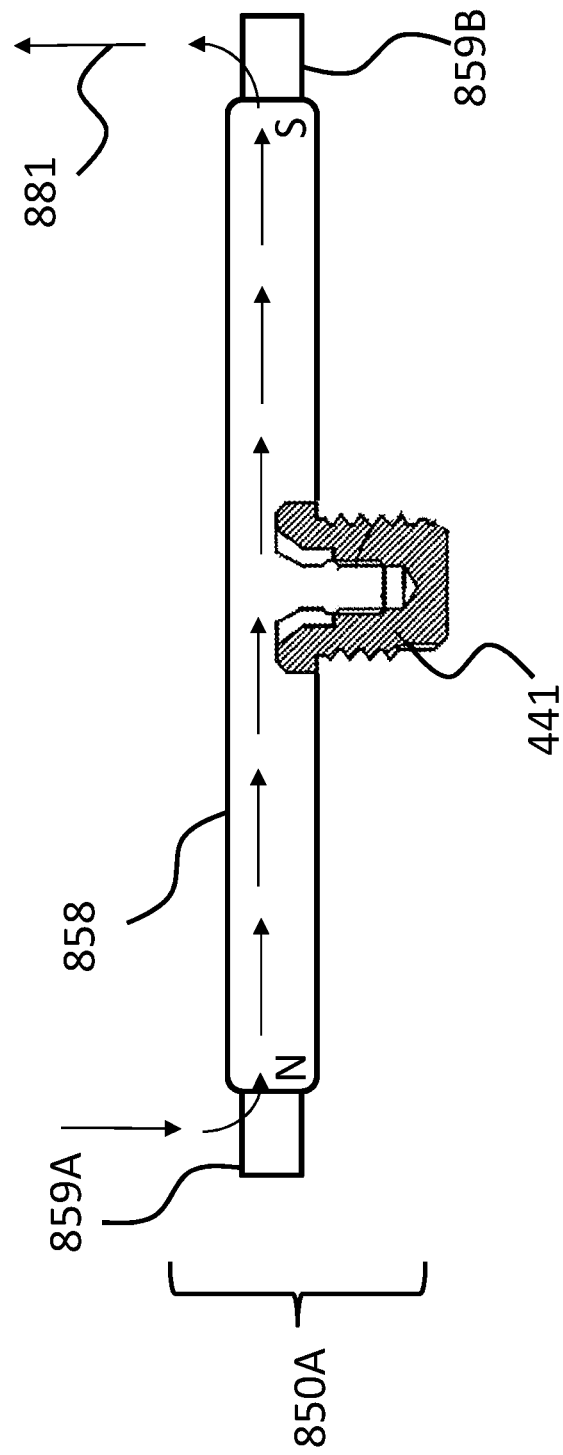
FIG. 8 is a schematic diagram of a portion of another exemplary magnetic flux circuit of a retention system according to an exemplary embodiment.

Further, FIG. 8 depicts another alternate embodiment of an implantable component, implantable component 850A, which utilizes a magnet arrangement (a single bar magnet 858, although multiple magnets can be used) where the North-South pole axis is parallel to the surface of the skull/perpendicular to the longitudinal axis of the bone conduction device. As can be seen, the implantable component 850A includes yokes 859A and 859B, while in some embodiments, a single yoke is used (the yoke surrounds the bar magnet 858) or no yoke(s) are used. FIG. 8 depicts a portion of a flux circuit 881, which is identical to that of flux 681 of FIG. 6, except as to how the flux is channeled through the implantable component of FIG. 8 as shown. In an exemplary embodiment, yokes 859A and 859B are made of soft iron (which can be encapsulated in another material). Thus, in an exemplary embodiment, the exemplary passive transcutaneous bone conduction device includes an implantable component having a permanent magnet having a North-South pole axis, wherein the implantable component is configured such that the North-South pole axis is parallel to bone of the recipient when the implantable component is implanted and attached to bone of a recipient.

It is noted that in an exemplary embodiment, the implantable component can be configured such that the permanent magnets thereof and/or the yoke(s) are contained in a housing. In an exemplary embodiment, the housing can be a hermetically sealed housing that hermetically isolates the permanent magnets and/or yoke(s) from body fluid of the recipient.

An exemplary embodiment is directed towards how the magnetic flux used to retain the external components 440A and 440B to the recipient via the implantable component (450A and 450B, respectively) interacts (or again, does not interact) with the magnetic fluxes of the actuator. For example, in an exemplary embodiment, there is an external component of a medical device (e.g., external component 440A or 440B) comprising an actuator 480 including a static magnetic flux path that reacts with a dynamic magnetic flux path to actuate the actuator. The external component further includes a magnetic retention system (e.g., utilizing magnets 458A and 458B) configured to retain the external components 440A and 440B to a recipient via interaction with a ferromagnetic component attached to a recipient (e.g., the permanent magnets and/or soft iron components of the implantable components 450A and 450B), and the magnetic retention system including a magnetic flux path circuit (e.g., flux path 681 of FIG. 6 or as modified in view of FIG. 7 or 8) that encircles the static magnetic flux path circuit(s) of the actuator. In an exemplary embodiment, the circuit of the retention system encapsulates the flux path circuits of the actuator.

The arrangement of FIGS. 4A and 4B in view of FIG. 5 can further be described as a bone conduction device including an external component (440A, 440B) thereof, including an actuator (the actuator of actuator assembly 480), which includes permanent magnets (558A and 558B) and a permanent magnet (448A and/or 448B) separate from the actuator. The permanent magnet generates a permanent magnetic field (681) having a component (e.g., the component flowing through one of the permanent magnets 458A and 458B) located outside the actuator on substantially opposite sides of the actuator. This permanent magnetic field enables the removable attachment of the external component (440A, 440B) to a recipient via interaction of the permanent magnetic field 681 with ferromagnetic material of an implanted component (450A, 450B).

Figure 9:
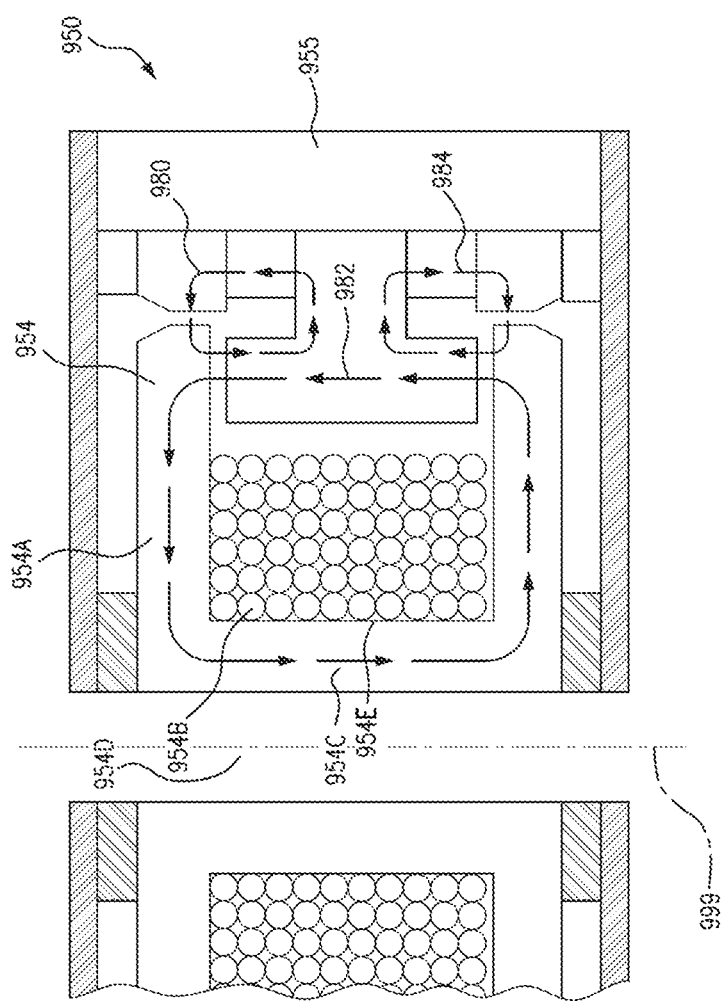
FIG. 9 is a schematic diagram of exemplary magnetic flux circuits of an actuator according to an exemplary embodiment.

Additional details of this exemplary embodiment will be described below, but first, magnetic flux path circuits of an exemplary actuator will be detailed so as to put this embodiment into perspective. Specifically, FIG. 9 details an exemplary static and magnetic flux path of an exemplary transducer 950 having a principle of operation corresponding to that of transducer 550 detailed above, and used in the actuator assembly 480. More specifically, FIG. 9 depicts a portion of an electromagnetic transducer 950. The electromagnetic transducer 950 is identical to electromagnetic transducer 550 detailed above, with the exception that there is no bobbin extension 554E, and the components in proximity thereto are adjusted accordingly (e.g., the spacer and the bottom spring are extended). In other embodiments, electromagnetic transducer 950 can correspond exactly to any of the electromagnetic transducers detailed herein and/or variations thereof. In this regard, the teachings below can be applicable, in at least some embodiments, to any of the electromagnetic transducers detailed herein and/or variations thereof unless otherwise specified, as is the case in the broader context that any of the specific teachings detailed herein and/or variations thereof can be applicable to any of the embodiments detailed herein and/or variations thereof unless otherwise specified.

As with bobbin assembly 554, bobbin assembly 954 is configured to generate a dynamic magnetic flux when energized by an electric current. In this exemplary embodiment, bobbin 954A is made of a material that is conducive to the establishment of a magnetic conduction path for the dynamic magnetic flux. Additional aspects of this feature are described in greater detail below.

FIG. 9 depicts the respective static magnetic flux 980 and static magnetic flux 984 of permanent magnets 558A and 558B (like components of FIG. 5 not being labeled for clarity), and dynamic magnetic flux 982 of the coil in the electromagnetic transducer 950 when the coil is energized according to a first current direction and when bobbin assembly 954 and counterweight assembly 955 are at a balance point with respect to magnetically induced relative movement between the two (hereinafter, the "balance point"). (When the current is reversed, the direction of the dynamic magnetic flux 982 is reversed.) That is, while it is to be understood that the counterweight assembly 955 moves in an oscillatory manner relative to the bobbin assembly 954 when the coil is energized, there is an equilibrium point at the fixed location corresponding to the balance point at which the counterweight assembly 954 returns to relative to the bobbin assembly 954 when the coil is not energized. It is noted that when the current direction is reversed, the direction of the dynamic magnetic flux is reversed from that depicted in FIG. 9

It is noted that as with all the figures depicting magnetic fluxes, FIG. 9 does not depict the magnitude/scale of the magnetic fluxes. In this regard, it is noted that in some embodiments, at the moment that the coil is energized and when bobbin assembly 954 and counterweight assembly 955 are at the balance point, relatively little, if any, static magnetic flux flows through the core of the bobbin 954A/the hole of the coil formed as a result of the coil being wound about the core of the bobbin 954A. Accordingly, FIG. 9 depicts this fact. However, in some embodiments, it is noted that during operation, the amount of static magnetic flux that flows through these components increases as the bobbin assembly 954 travels away from the balance point (both downward and upward away from the balance point) and/or decreases as the bobbin assembly 954 travels towards the balance point (both downward and upward towards the balance point).

It is noted that the directions and paths of the static magnetic fluxes and dynamic magnetic fluxes are representative of some exemplary embodiments, and, in other embodiments, the directions and/or paths of the fluxes can vary from those depicted.

Still referring to FIG. 9, it can be seen that the dynamic magnetic flux 982 travels through the bobbin core 954C about which coils 954B extend. In the embodiment of FIG. 9, because bobbin 954A is made of a magnetically permeable material (e.g., a highly permeable material), the bobbin core 954C is a magnetic core. In this regard, effectively all, if not all, of the dynamic magnetic flux 982 travels through the material of the bobbin 954A. That is, essentially no dynamic magnetic flux travels through the space 954D in the bobbin. In this regard, the electromagnetic transducer 550 is configured such that the effective dynamic magnetic flux travels through the material of bobbin 954A.

Figure 10:
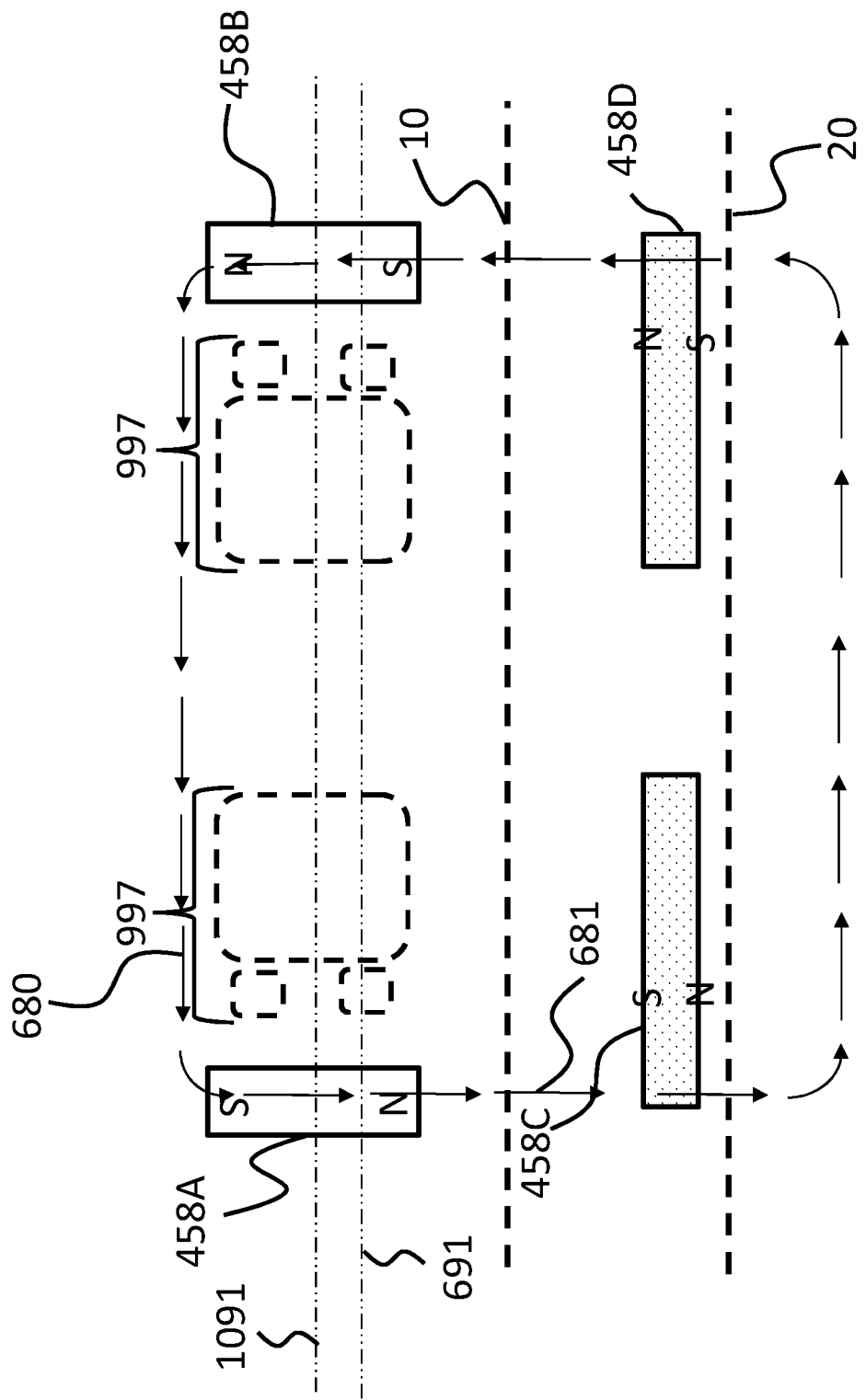
FIG. 10 is a schematic diagram depicting an exemplary magnetic flux circuit of an exemplary retention system combined with an exemplary magnetic flux circuit of an actuator according to an exemplary embodiment.

FIG. 10 depicts the magnetic flux path 681 generated by the permanent magnets 458A-458D of the magnetic retention system of FIG. 6 along with the static magnetic flux path 980 and static magnetic flux path 984 of permanent magnets 558A and 558B and the dynamic magnetic flux path 982 of the coil of the actuator used in the actuator assembly 480, collectively identified as actuator flux 997. As can be seen, the magnetic flux of the retention system encircles/goes around the magnetic fluxes of the actuator (the actuator flux 997).

Accordingly, as can be seen, the external component 440A according to some embodiments is configured to channel the magnetic flux of the magnetic retention system in a circuit around the actuator assembly 448, and thus the actuator thereof. Further, as can be seen from FIGS. 4A, 6 and 10, embodiments include an implantable component 450A of a passive transcutaneous bone conduction device comprising ferromagnetic material (whether it be a permanent magnet or soft iron or a combination thereof or other materials/components) configured to be totally implanted underneath skin of the recipient and attached to bone of the recipient. The passive transcutaneous bone conduction device is configured such that the magnetic flux circuit 681 of the magnetic retention system extends through skin of the recipient to the ferromagnetic material (e.g., permanent magnets 458C and 458D, etc.) of the implantable component 450A resulting in magnetic attraction between the external component 440A and the implantable component 450A, thereby removably retaining the external component 440A to the recipient.

Accordingly, an exemplary embodiment includes a magnetic retention flux path circuit that extends as will now be detailed, where the following is described in terms of an external component that includes yoke 460, although in an alternate embodiment, the yoke 460 is not present—that is, in some embodiments, there may or may not be a ferromagnetic component (yoke 460) extending from a first lateral location of the removable component proximate a first of the retention magnets 458B to a second lateral location of the removable component proximate a second of the retention magnets 458B. In an exemplary embodiment, there is a magnetic flux path circuit that is established by a plurality of retention magnets 458A and 458B, where the circuit extends from a first of the retention magnets (458B) to the ferromagnetic component 460, through the ferromagnetic component 460, from the ferromagnetic component 460 to the second of the retention magnets 458A, and from the second of the retention magnet 458A out of removable component beyond the recipient interface component (support assembly 466A or 466B) and then back into the removable component and then to the first retention magnet 458B.

In view of FIG. 10, an exemplary embodiment can be described as an external component 440A that is configured such that actuation of the actuator of the actuator assembly 480 moves a seismic mass (counterweight assembly 555) along a first direction (e.g., as represented by arrows 399 of FIG. 4A and 500A of FIG. 5) normal to a surface of a skin of a recipient of the device. The magnetic retention system of the external component includes a static magnetic flux circuit 681. The actuator of the external component includes one or more static magnetic fluxes and/or one or more dynamic magnetic fluxes. A plane normal to the first direction (represented by plane 691 of FIG. 10) bisects the flux circuit 681 of the retention system and the magnetic fluxes 997 of the actuator. In an exemplary embodiment, a plane normal to the first direction (represented by plane 1091 of FIG. 10) bisects the flux circuit 681 of the retention system and divides the magnetic fluxes 997 of the actuator in half. That is, the plane 1091 is located such that the fluxes of the actuator are located evenly above and below the plane, and the retention flux is bisected by the plane.

Figure 11:
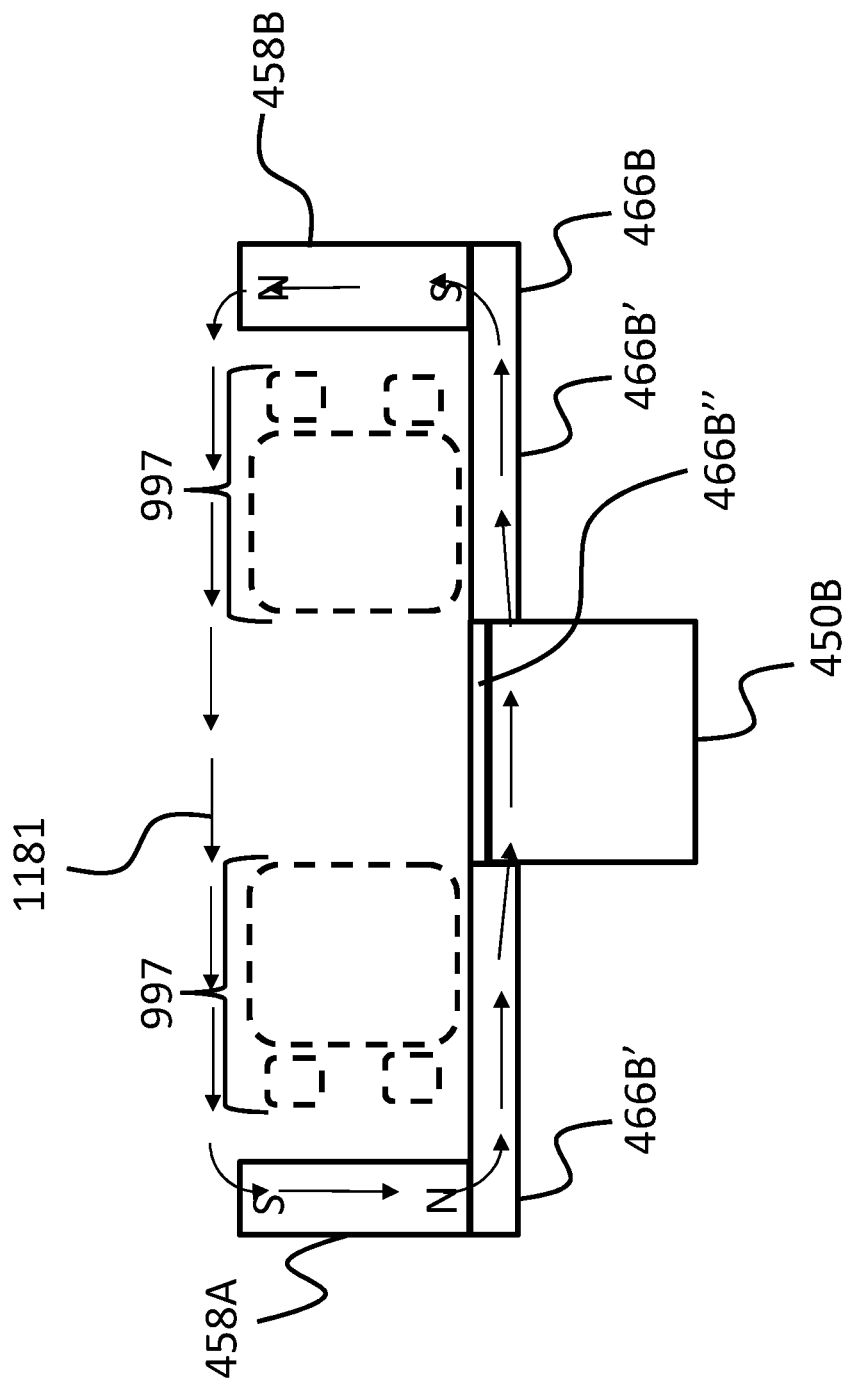
FIG. 11 is another schematic diagram depicting an exemplary magnetic flux circuit of an exemplary retention system combined with an exemplary magnetic flux circuit of an actuator according to an exemplary embodiment.

FIG. 11 depicts an exemplary static magnetic flux path of an exemplary magnetic retention system for the percutaneous bone conduction device 400B of FIG. 4B, along with the magnetic flux paths of the actuator, where the implantable component 450B is functionally represented in black-box format. Specifically, as can be seen, the magnetic flux path 1181 encircles the flux paths of the actuator (paths 997). While there are similarities between the flux path 1181 of the percutaneous bone conduction device 400B and the flux path of the magnetic retention system of the transcutaneous bone conduction device 400A, it can be seen that in an exemplary embodiment, flux path 1181 does not extend into the recipient/does not extend beneath the outer surface of the skin of the recipient. Moreover, in an exemplary embodiment, the support assembly 466B includes a component configured to channel the magnetic flux path 1181 to the implantable component 450B. More specifically, the support assembly 446B includes components 466B' (although in other embodiments, 466B' can be a single component) made of soft iron or other magnetic material that channels the magnetic flux path 1181 from the permanent magnet 458A to the implantable component 450B, which includes ferromagnetic material (e.g., a permanent magnet). From the implantable component 450B, the magnetic flux path 1181 is channeled through 466B' to the permanent magnet 458B.

As can be seen from FIG. 11, support assembly 446B includes element 466B". This is a component that is not conducive to channeling the magnetic flux 1181, thus "forcing" the magnetic flux path 1181 to travel to the implantable component 450B, or at least presenting a path that is less conducive to the conduction of the static flux path 1181 therethrough. That said, in an alternate embodiment, 466B" can instead also be soft iron or the like, the relative thinness of that section as compared to those of 466B' encouraging the magnetic flux path 1181 to travel to the implantable component 450B.

It is noted that in at least some embodiments, not all of the magnetic flux of the retention system of the percutaneous bone conduction device is channeled to the implantable component 450B (just as in at least some embodiments not all of the magnetic fluxes retention system of the passive transcutaneous bone conduction device 400A travels to the implantable component). Some of this flux can bypass the implantable component 450B. Still, sufficient magnetic attraction between the removable component 440B and the implantable component 450B exists to removably retain the removable component 440B to the implantable component 450B.

Accordingly, in view of FIGS. 4B and 11, an exemplary embodiment includes a percutaneous bone conduction device, comprising an external component 440B and a percutaneous implant 450B of the percutaneous bone conduction device including ferromagnetic material configured to be connected to bone of a recipient and to extend through skin of the recipient. The percutaneous bone conduction device 400B is configured such that the magnetic flux 1181 of the magnetic retention system extends to the ferromagnetic material of the percutaneous implant, resulting in magnetic attraction between the external component 440B and the percutaneous implant, thereby removably retaining the external component 440B to the recipient.

Further, as can be seen, the percutaneous bone conduction device 400B includes a permanent magnetic field (flux 1181) that travels in a circuit that passes through at least one permanent magnet (458A and/or 458B) and the ferromagnetic material of the implantable component 450B and encircles the actuator of actuator assembly 480, thereby removably attaching the external component 440B to the recipient. Thus, an exemplary embodiment includes an external component including a plurality of retention magnets that generate a magnetic field having a circuit 681 that retains the external component to the recipient. The actuator of that external component, being an electromagnetic actuator having a static magnetic field circuit that interacts with a dynamic magnetic field circuit to actuate the actuator, is arranged (or, more accurately, the external component is arranged) such that the static magnetic field circuit and the circuit that retains the external component to the recipient have completely separate paths. That is, no parts of the paths overlap one another. That said, in such an embodiment, the fluxes can interact, providing that the circuits to not cross one another (in the embodiments depicted herein, one circuit encircles the other).

As noted above, an exemplary embodiment is such that the magnetic flux of the permanent magnets of the magnetic retention system of the bone conduction devices encircles the actuator of the actuator assembly 480 (or other transducer used in a medical device other than a bone conduction device). In an exemplary embodiment, there is no interaction between the magnetic field of the retention system and the magnetic fields of the actuator. By no interaction, it is meant that at most, only trace amounts of the magnetic flux of the retention system interacts with the fluxes of the actuator. This is as a result of trace amounts of the flux of the retention system entering the actuator and/or trace amounts of the fluxes of the actuator escaping the actuator. That said, in an exemplary embodiment, effectively no interaction between the flux of the retention system and the fluxes of the actuator interact with one another. In this regard, more than trace amounts of the fluxes can interact with each other, providing that the interaction enables the bone conduction device to effectively evoke a hearing percept while being held to the recipient via the magnetic retention system. In an exemplary embodiment, the path of the magnetic field of the retention system follows a path where the strongest field strength of that path is present where the maximum field strength of the fluxes of the actuator is only 30%, 25%, 20%, 15%, 10%, 5% or 0% or any value or range of values therebetween in 1% increments of the maximum field strength of the static magnetic field(s) when the coil of the actuator is not energized.

In an exemplary embodiment, the permanent magnets of the retention system are such that the seismic mass of the actuator is moved no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 micrometers from the equilibrium point (i.e., the location where the seismic mass is stationary in the absence of a dynamic magnetic flux), which could be the balance point of a balanced actuator, in the presence of the permanent magnets of the retention system of the external component relative to that which would be the case in the absence of the permanent magnets of the retention system of the external component. That is, for example, placement of the permanent magnets in the external component (e.g., magnets 458A and 458B) can result in a magnetic field that moves the seismic mass no more than about 5 micrometers from its equilibrium point.

In an exemplary embodiment, at least about 50%, 55%, 60%, 65%, 70%, 75%, 80%, 85%, 90%, 95% or about 100%, or any value or range of values therebetween in about 1% increments, of the magnetic flux of the retention system occupies space where at most, only trace amounts, if any, of the static magnetic fluxes of the actuator are present.

In an exemplary embodiment, the removable external components are such that a magnetic saturation level of functional components of the actuator is at least approximately on the same level in the presence of the retention system as that which would be the case in the absence of the retention system (i.e., the removal of the permanent magnets 448A and 448B).

In view of the above, an exemplary embodiment is such that substantially all of the magnetic flux of the magnetic retention system is separated from the static magnetic flux path of the actuator. In an exemplary embodiment, the dynamic magnetic flux of the actuator is such that the dynamic magnetic flux is effectively isolated from interaction with the magnetic field of the retention system.

Further, in view of the above, an exemplary embodiment includes an external component for a bone conduction system comprising an actuator including a static magnetic flux path that reacts with a dynamic magnetic flux path to actuate the actuator and a magnetic retention system configured to retain the external component to a recipient via interaction with a ferromagnetic component attached to a recipient, the magnetic retention system including a magnetic flux path that encapsulates the static magnetic flux path of the actuator.

Figure 12:
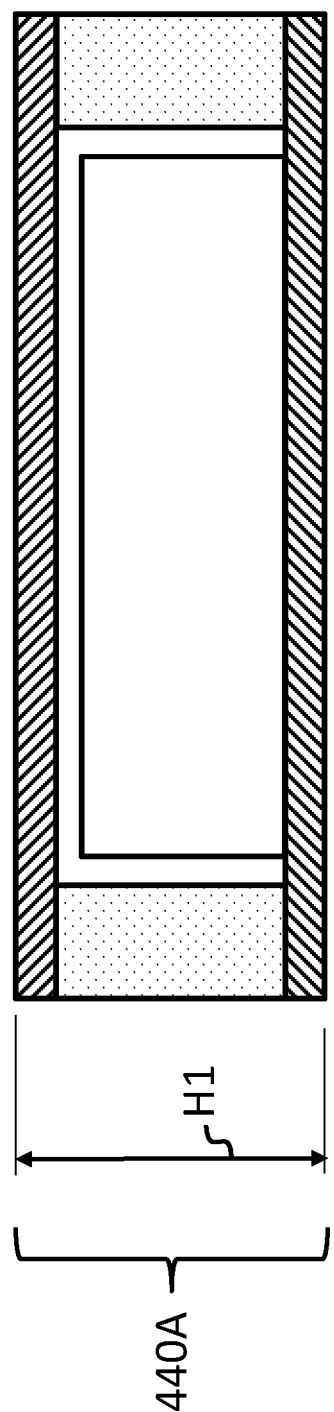
FIG. 12 depicts a height dimension of the external component of FIG. 4A.

Embodiments of at least some of the teachings detailed herein and/or variations thereof can have utility in that it provides a compact external device. More specifically, referring to FIG. 12, external component 440A is again depicted. FIG. 12 depicts the overall height H1 of the external component 440A, as dimensioned from a first surface of external component configured to contact skin of the recipient (e.g., the recipient interface component corresponding to the bottom of support assembly 446A) to the top of the external component (which can correspond to the top of the yoke 460 or a portion of the housing of the external component that covers the yoke 460 (if present) or otherwise houses the permanent magnet(s) of the retention system and the actuator assembly 480). In an exemplary embodiment, the height H1 is no more than about 7 mm, 8 mm, 9 mm, 10 mm, 11 mm, 12 mm, 13 mm, 14 mm or about 15 mm.

Accordingly, an exemplary embodiment includes an external component that includes a first surface configured to contact skin of the recipient (e.g., the bottom surface of support assembly 460A) through which vibrations generated by the actuator are conducted into skin of the recipient. A height of the external component as dimensioned from the first surface is no more than about fifteen millimeters.

In at least some embodiments, the distance between the aforementioned first surface configured to contact skin of the recipient to the center of mass/center of gravity of the external component 740A is no more than about 3 mm, 4 mm, 5 mm, 6 mm, 7 mm, 8 mm, 9 mm or about 10 mm.

In at least some exemplary embodiments, the aforementioned height values alone and/or in combination with the reduced overall weight of the external component can have utility in that the lever effect can be reduced relative to that which might otherwise be the case without the aforementioned features without decreasing performance, again relative to that which might otherwise be the case without the aforementioned features. By way of example only, and not by way limitation, by reducing the lever effect, the peak pressures at the bottom portions of the pressure plate relative to the direction of gravity can be reduced (e.g., because the moment about the external component resulting from the mass thereof and/or the distance of the center of gravity/center of mass thereof from the skin is reduced relative to that which would otherwise be the case). In an exemplary embodiment, this can reduce the chances of necrosis, or the like, and/or reduce the sensation of pinching, or the like, relative to that which would be the case for the aforementioned alternate configuration.

It is noted that in at least some embodiments, the magnetic field of the retention systems are channeled about electronic circuitry of the removable components to limit interaction therewith. That is, the magnetic field of the retention systems can interfere with the electronic circuitry of the medical devices (e.g., a sound processor of a bone conduction device, the recording apparatus of a telemetry device of a medical device, etc.). Accordingly, in an exemplary embodiment, the external components are configured such that the circuit in which the magnetic flux of the magnetic retention system flows is isolated from the electronic circuitry of the removable component, even when the circuitry is located between magnet 458A and 458B (e.g., where actuator assembly 448 is located).

Figure 13:
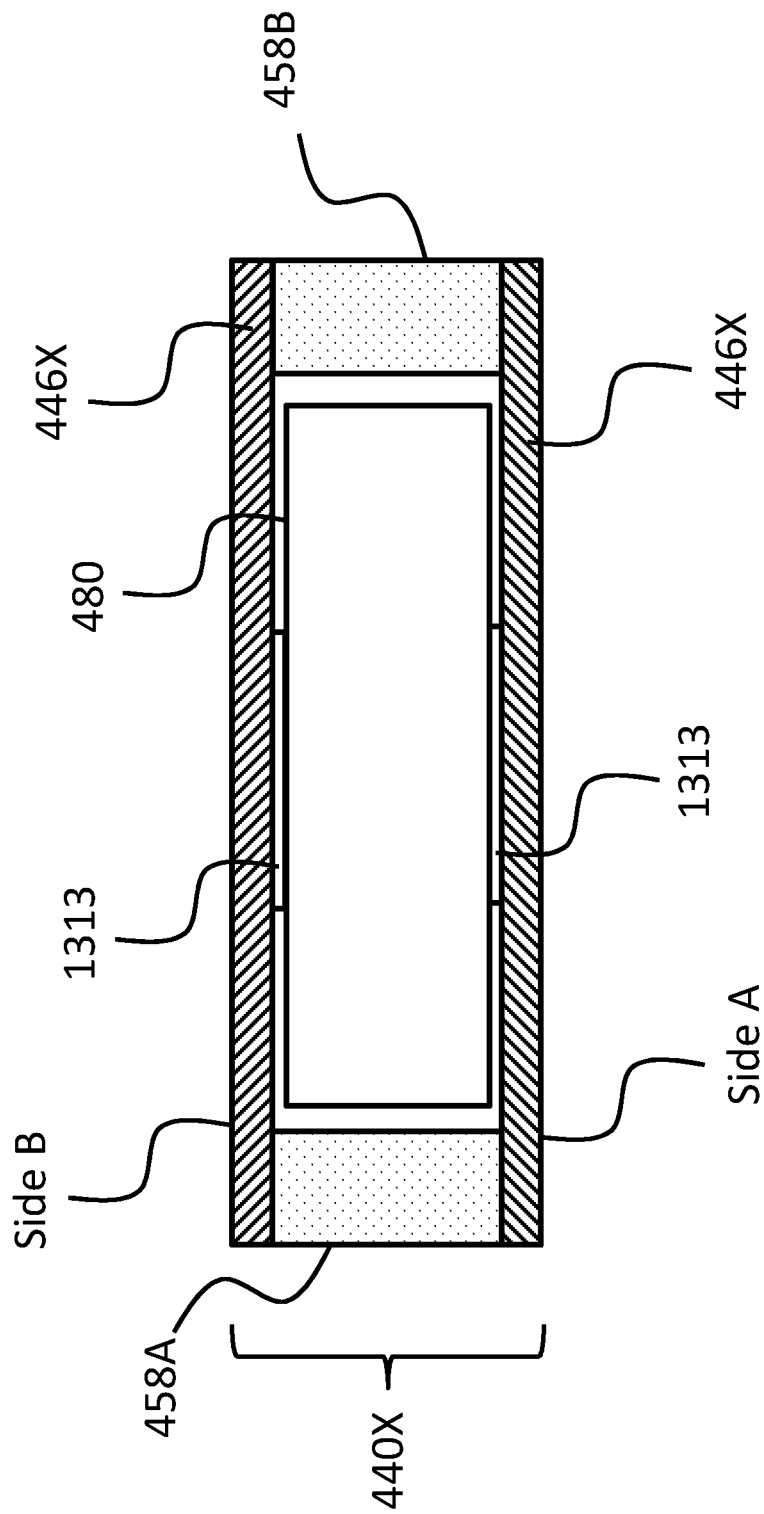
FIG. 13 depicts an alternate embodiment of an external component.

Referring now to FIG. 13, it is seen that there is an exemplary external component 440X which is a quasi-black box functional depiction of an external component usable with a passive transcutaneous bone conduction system and a percutaneous bone conduction system, depending on the recipient interface arrangement as will be detailed below. External component 440X includes permanent magnets 458A and 458B as detailed above with respect to 440A and 440B. The configuration of external component 440X is such that it is left-right compatible with little or no modification. That is, external component 440X can be placed on the left side of the recipient or the right side of the recipient (providing that the implantable component is present). In an exemplary embodiment, this is achieved by simply flipping over the external component 440X. That is, in an exemplary embodiment, side "A" is utilized for the recipient interface if the implant is located on the left side of the recipient, and side "B" is utilized for the recipient interface if the implant is located on the right side of the recipient. Accordingly, an exemplary embodiment, the external component 440X includes two recipient interfaces 446X. As can be seen, the actuator assembly 480 is placed into vibrational communication with the recipient interfaces 446X via components 1313.

In an exemplary embodiment, the external component 440X is configured such that it is structurally substantially symmetric about the plane normal to the longitudinal axis. That said, as will be detailed below, in an alternative embodiment, the external component 440X is not structurally substantially symmetric.

In an exemplary embodiment, this can be achieved because the magnetic flux circuit of the permanent magnets 458A and 458B encircle the actuator 480. More particularly, the component of the magnetic flux circuit that passes through side "A" can be substantially identical to that which passes through side "B," (albeit the direction of the magnetic flux is reversed) at least when the external component 440X is located away from any other magnetic components. Accordingly, in an exemplary embodiment, there is no yoke 460 of magnetically conductive material to channel the magnetic flux from one of the permanent magnets of the other permanent magnet. Instead, both recipient interfaces 446X are made at least in part of magnetically nonconductive material such that the magnetic fluxes are not influenced thereby, or at least such that the magnetic fluxes can be utilized to achieve the left-right compatibility. Indeed, with respect to the latter, the recipient interfaces 446X can have magnetically conductive material extending from the permanent magnets towards the center of the recipient interfaces that can to the arrangement of the support assembly 446B of external component 446B. Accordingly, as noted above, in an exemplary embodiment, the external component 440X is substantially structurally symmetric about the plane normal to the longitudinal axis. Of course, there may be components that are located on one side a plane that are not located on the other, such as by way of example only and not by way of limitation, the sound processor, a microphone, etc. Still these are relatively minor components with respect to the overall weight of the external component 440X. Thus, the external component 440X is still substantially structurally symmetric about the aforementioned plane.

That said, in an alternate embodiment, a variation of the external component 440X can be configured such that includes a yoke 460 that is movable from side "B" to side "A" and visa-versa. In an exemplary embodiment, the yoke 460 can be located over the recipient interface of a given side. Alternatively, the recipient interface of one side can be replaced by the yoke, and the yoke can be replaced by a recipient interface. Any device, system and/or method that can enable the left-right compatibility can be utilized in at least some embodiments.

It is noted that any disclosure of an apparatus or system herein corresponds to a method of utilizing that device and/or system. By way of example only and not by way of limitation, with respect to the just detailed external component 440X, a method can include placing a bone conduction device 440X onto a recipient on a first side of the recipient and evoking a hearing percept, and then placing the bone conduction device 440X onto that same recipient on a second side the recipient opposite the first side the recipient and also evoking a hearing percept. In an exemplary embodiment, this method is performed without modifying the external component 440X. in an alternate embodiment, this method is performed by a rearranging components of the external component 440X that are removably attached to the other components of the external component 440X (e.g., the yoke 460).

It is further noted that any method of manufacture described herein constitutes a disclosure of the resulting product, and any description of how a device is made constitutes a disclosure of the corresponding method of manufacture. Also, it is noted that any method detailed herein constitutes a disclosure of a device to practice the method, and any functionality of a device detailed herein constitutes a method of use including that functionality.

While various embodiments of the present invention have been described above, it should be understood that they have been presented by way of example only and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:
1. A hearing prosthesis, comprising:
a component, including:
a plurality of magnets, wherein
the plurality of magnets collectively form a circular shape and are configured to establish magnetic attraction between an external component and an implantable component of the hearing prosthesis sufficient to hold the external component against skin of a recipient,
the plurality of magnets includes at least a first magnet and second magnet,
the first magnet has a North-South pole axis, the second magnet has a North-South pole axis extending in a different direction from the North-South pole axis of the first magnet,
the component is the implantable component of the hearing prosthesis, and the component is configured to channel a magnetic flux from the first magnet to the second magnet, the magnetic flux establishing the magnetic attraction.

2. The hearing prosthesis of claim 1, wherein:
the hearing prosthesis is configured so that the North-South pole axes of the first magnet and the second magnet are normal to a surface of a skull of the recipient and/or normal to a surface of the skin of the recipient at least when the external component is held against the skin of the recipient.

3. The hearing prosthesis of claim 1, wherein:
the first magnet is spaced away from the second magnet.

4. The hearing prosthesis of claim 1, further comprising:
a sound processor and a microphone.

5. The hearing prosthesis of claim 1, wherein:
the hearing prosthesis also includes the external component.

6. The hearing prosthesis of claim 1, further comprising:
the external component of the hearing prosthesis.

7. A hearing prosthesis, comprising:
a component, including:
    a plurality of magnets, wherein
    the plurality of magnets collectively form a circular shape and are configured to establish magnetic attraction between an external component and an implantable component of the hearing prosthesis sufficient to hold the external component against skin a recipient, wherein the component is one of the external component or the implantable component,
    the plurality of magnets includes at least a first magnet and second magnet,
    the first magnet has a North-South pole axis,
    the second magnet has a North-South pole axis extending in a different direction from the North-South pole axis of the first magnet, and
    at least one of:
        (i) the component is configured to redirect, within the component, magnetic flux from the first magnet in a direction normal to the North-South pole axis of the second magnet; or
        (ii) the component is configured to redirect, within the component, magnetic flux from the first magnet in a direction parallel to a surface of the skin of the recipient at least when the external component is held against the skin of the recipient.

8. The hearing prosthesis of claim 7, wherein:
the component is the external component of the hearing prosthesis.

9. The hearing prosthesis of claim 7, wherein one of:
i. the first magnet is half-circular shaped, and the second magnet is half-circular shaped; or
ii. the first magnet is semi-circular shaped, and the second magnet is semi-circular shaped.

10. The hearing prosthesis of claim 9, wherein:
the first magnet is semi-circular shaped, and the second magnet is semi-circular shaped.

11. The hearing prosthesis of claim 7, wherein:
the component is configured to redirect, within the component, magnetic flux from the first magnet in the direction parallel to the surface of the skin of the recipient at least when the external component is held against the skin of the recipient.

12. The hearing prosthesis of claim 7, wherein the component is the implantable component, and the hearing prosthesis further comprises:
the external component of the hearing prosthesis, wherein the external component of the hearing prosthesis includes:
    a third magnet having a North-South alignment in a third direction, a fourth magnet having a North-South alignment in a fourth direction different from the third direction, and magnetic material attached to the third magnet and to the fourth magnet, wherein the third magnet is partially circular shaped and the fourth magnet is partially circular shaped.

13. The hearing prosthesis of claim 7, wherein:
the component is configured to redirect, within the component, magnetic flux from the first magnet in the direction normal to the North-South pole axis of the second magnet.

14. The hearing prosthesis of claim 7, wherein:
the hearing prosthesis includes the external component and the implantable component.

15. A hearing prosthesis, comprising:
a component, including:
    a plurality of magnets, wherein
    the plurality of magnets collectively form a circular shape and are configured to establish magnetic attraction between an external component and an implantable component of the hearing prosthesis sufficient to hold the external component against skin of a recipient, wherein the component is one of the external component or the implantable component,
    the plurality of magnets includes at least a first magnet and second magnet,
    the first magnet has a North-South pole axis,
    the second magnet has a North-South pole axis extending in a different direction from the North-South pole axis of the first magnet, and
    the component further includes a ferromagnetic component attached to the first magnet and the second magnet.

16. The hearing prosthesis of claim 15, wherein:
the component is configured to channel a magnetic flux from the first magnet to the second magnet, the magnetic flux establishing the magnetic attraction.

17. The hearing prosthesis of claim 15, wherein the ferromagnetic component is a permanent magnet.

18. The hearing prosthesis of claim 17, further comprising:
a sound processor and a microphone.

19. The hearing prosthesis of claim 15, wherein the ferromagnetic component channels magnetic flux generated by at least the first magnet in a direction normal to a longitudinal axis of the component.

20. The hearing prosthesis of claim 15, wherein the component is the implantable component, and further comprising the external component, wherein
    the external component includes a third magnet and a fourth magnet,
    the third magnet has a North-South alignment, and
    the fourth magnet has a North-South alignment in a different direction from the North-South alignment of the third magnet.

21. The hearing prosthesis of claim 15, wherein the component is the external component, and wherein the hearing prosthesis further comprises the implantable component.

22. The hearing prosthesis of claim 15, wherein:
the hearing prosthesis includes the external component and the implantable component.

23. A hearing prosthesis, comprising:
an external component; and
an implantable component, including:
  a first magnet having a North-South alignment in a first direction; and
  a second magnet having a North-South alignment in a second direction different from the first direction, wherein
  the first direction is fixed relative to the second direction, and
  the implantable component is configured to retain the external component of the hearing prosthesis on a recipient of the hearing prosthesis via magnetic coupling between the first and second magnet of the implantable component and one or more permanent magnets of the external component, wherein
the external component of the hearing prosthesis includes:
  a third magnet having a North-South alignment in a third direction, a fourth magnet having a North-South alignment in a fourth direction different from the third direction, and magnetic material attached to the third magnet and to the fourth magnet, wherein the third magnet is partially circular shaped and the fourth magnet is partially circular shaped.

24. The hearing prosthesis of claim 23, wherein:
the first direction is parallel to the second direction.

25. The hearing prosthesis of claim 23, wherein:
the North-South alignment of the second magnet is opposite to the North-South alignment of the first magnet.

26. The hearing prosthesis of claim 23, wherein:
the first magnet is half-moon shaped and the second magnet is half-moon shaped.

27. The hearing prosthesis of claim 23, wherein:
the third magnet is spaced apart from the fourth magnet.

28. The hearing prosthesis of claim 23, further comprising:
a sound processor and a microphone.

29. The hearing prosthesis of claim 23, wherein:
the third direction is parallel to the fourth direction.

30. The hearing prosthesis of claim 23, wherein:
the external component is configured to channel magnetic flux generated by the third magnet from the third magnet to the fourth magnet within the external component.

31. A hearing prosthesis, comprising:
an external component; and
an implantable component, including:
  a first magnet having a North-South alignment in a first direction; and
  a second magnet having a North-South alignment in a second direction different from the first direction, wherein
  the first direction is fixed relative to the second direction, and
  the implantable component is configured to retain the external component of the hearing prosthesis on a recipient of the hearing prosthesis via magnetic coupling between the first and second magnet of the implantable component and one or more permanent magnets of the external component, wherein
the one or more permanent magnets comprise a third magnet and a fourth magnet,
the third magnet has a North-South alignment,
the fourth magnet has a North-South alignment in a different direction from the North-South alignment of the third magnet, and
the external component further includes a ferromagnetic component extending from the third magnet to the fourth magnet.

32. The hearing prosthesis of claim 31, wherein the ferromagnetic component is a permanent magnet.

33. The hearing prosthesis of claim 31, wherein the ferromagnetic component extends normal to a longitudinal axis of the external component.

34. The hearing prosthesis of claim 31, wherein the ferromagnetic component channels magnetic flux generated by at least the third magnet in a direction horizontally to the fourth magnet.

35. The hearing prosthesis of claim 31, wherein:
a cross-section of the third magnet has an outer profile that has a length and a width, the length being longer than the width; and
the North-South pole axis of the third magnet is parallel to the length.

36. The hearing prosthesis of claim 31, further comprising:
electronics.

* * * * *